United States Patent [19]
Starostovic

[11] Patent Number: 6,053,052
[45] Date of Patent: *Apr. 25, 2000

[54] PANEL PERFORMANCE TEST SYSTEM

[75] Inventor: Edward J. Starostovic, Stoughton, Wis.

[73] Assignee: Timberco, Inc., Madison, Wis.

[*] Notice: This patent is subject to a terminal disclaimer.

[21] Appl. No.: 08/991,119

[22] Filed: Dec. 16, 1997

Related U.S. Application Data

[63] Continuation-in-part of application No. 08/558,356, Nov. 16, 1995, Pat. No. 5,699,274.

[51] Int. Cl.$^7$ ........................................................ G01N 3/10
[52] U.S. Cl. ................................................ 73/851; 73/852
[58] Field of Search ............................. 73/849, 851, 852, 73/853, 855

[56] References Cited

U.S. PATENT DOCUMENTS

| | | |
|---|---|---|
| 2,439,130 | 4/1948 | Firestone . |
| 2,506,048 | 5/1950 | Van Den Akker ........................ 73/852 |
| 3,194,063 | 7/1965 | McKean . |
| 3,423,991 | 1/1969 | Collins . |
| 3,504,532 | 4/1970 | Muenow et al. . |
| 3,512,400 | 5/1970 | Lynnworth . |
| 3,513,690 | 5/1970 | Pellerin et al. . |
| 3,858,437 | 1/1975 | Jarzynski et al. . |
| 3,861,200 | 1/1975 | Dory . |
| 3,888,108 | 6/1975 | Brands . |
| 4,147,064 | 4/1979 | Bond . |
| 4,201,093 | 5/1980 | Logan . |
| 4,213,349 | 7/1980 | Miura . |
| 4,313,348 | 2/1982 | Madsen . |
| 4,338,820 | 7/1982 | Jassby et al. . |
| 4,481,820 | 11/1984 | Thomann . |
| 4,492,117 | 1/1985 | Chubachi . |
| 4,589,288 | 5/1986 | Porter et al. . |
| 4,838,085 | 6/1989 | Pellerin et al. . |
| 4,926,694 | 5/1990 | Crews, Jr. et al. . |
| 4,982,609 | 1/1991 | Talley, III . |
| 5,060,516 | 10/1991 | Lau et al. . |
| 5,127,271 | 7/1992 | Sato et al. . |
| 5,187,987 | 2/1993 | Anderson et al. . |
| 5,237,870 | 8/1993 | Fry et al. . |
| 5,423,991 | 6/1995 | Collins . |
| 5,503,024 | 4/1996 | Bechtel et al. ............................ 73/849 |
| 5,583,298 | 12/1996 | Walsh ....................................... 73/852 |
| 5,616,848 | 4/1997 | Hemingway et al. .................... 73/838 |
| 5,699,274 | 12/1997 | Starostovic, Jr. ......................... 73/849 |
| 5,804,738 | 9/1998 | Bach et al. ............................... 73/852 |

FOREIGN PATENT DOCUMENTS 918286  1/1973  Canada .

OTHER PUBLICATIONS

Voluntary Product Standard PS–2.
*Sensors and Analyzer Handbook,* H.N. Norton, Prentice–Hall, Inc. (1982) pp. 93–96.
ASTM E661–88, Standard Test Measure for Performance of Wood and Wood–Based Floor and Roof Sheathing Under Concentrated Static and Impact Loads.

*Primary Examiner*—Max Noori
*Attorney, Agent, or Firm*—Michael Best & Friedrich LLP

[57] ABSTRACT

The invention is a performance testing system for wood-based panels. The testing includes performance of a material under a load concentrated in a single area, performance of edge support systems under a concentrated load and performance of a material under static bending conditions. The system is computerized and automatically applies a load to a panel to be tested, reads and records deflection of the panel without operator involvement, and provides a printed test report.

18 Claims, 27 Drawing Sheets

```
                                    Date:
                                    Time:          14:32
                                    Control ID:       54

CONCENTRATED LOAD AND DEFLECTION TEST RESULTS
                              ABC Company Inspector:                                    Material:    OSB
End Use/Span Rating:   Roof - 24              Thickness:   7/16"

Maximum Deflection Under 200 lbf Load

Deflection Load (lbs.):                    200
        Actual Deflection (in.):                 0.407
        Permitted Maximum Deflection (in.):      0.469

Test Result:                       |  Pass  |

Minimum Ultimate Load

Applied Load (lbs.):                       386
        Required Minimum Ultimate Load (lbs.):     400

Test Result:                       |  Fail  |
```

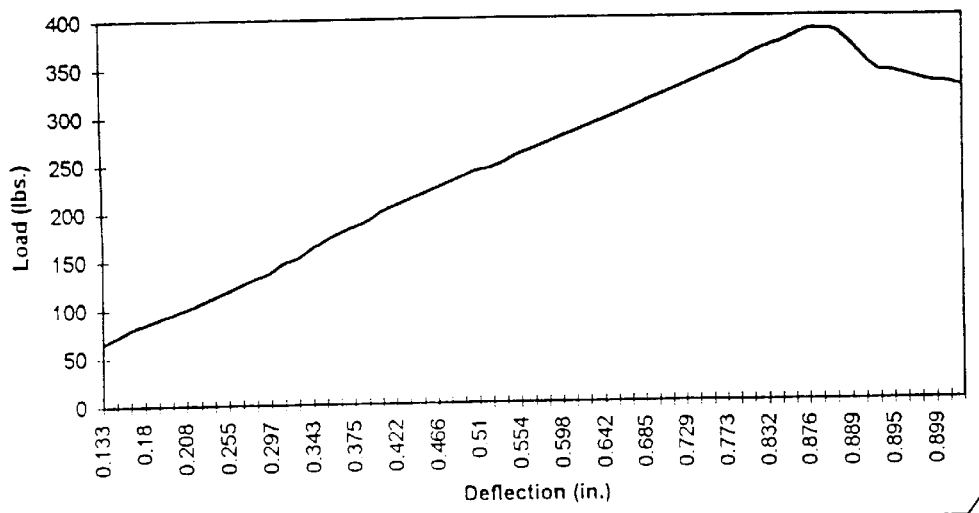

FIG. 31

```
                                        Date:
                                        Time:        14:52
                                        Control ID:     53
```

CONCENTRATED LOAD AND DEFLECTION TEST RESULTS

Inspector:  
End Use/Span Rating: SubFloor - 24

Material: OSB  
Thickness: 23/32"

Maximum Deflection Under 200 lbf Load

Deflection Load (lbs.): 201  
    Actual Deflection (in.): 0.214  
    Permitted Maximum Deflection (in.): 0.250

Test Result: | Pass |

Minimum Ultimate Load

Applied Load (lbs.): 400  
    Required Minimum Ultimate Load (lbs.): 400

Test Result: | Pass |

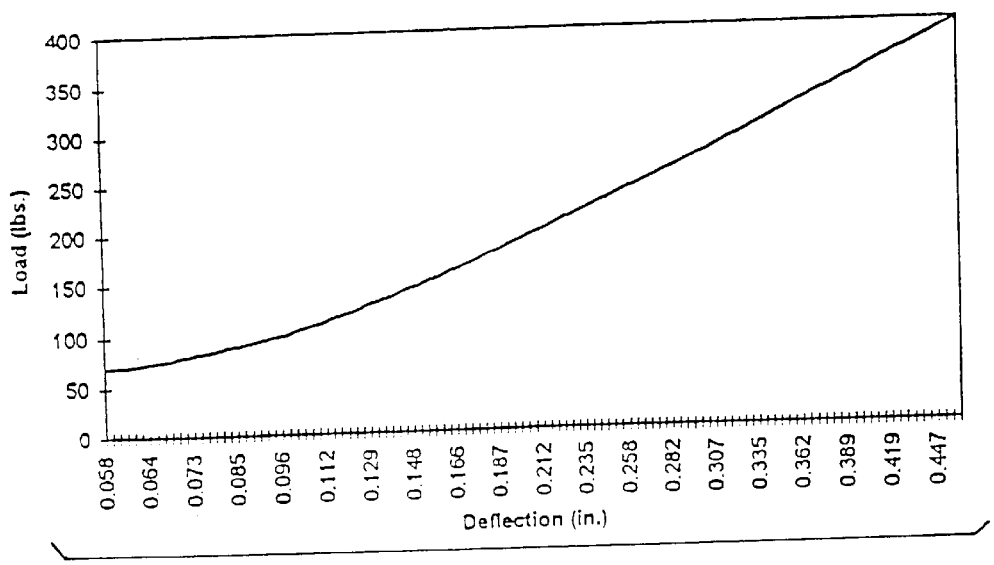

FIG. 32

PANEL PERFORMANCE TEST SYSTEM

CROSS-REFERENCE TO RELATED APPLICATIONS

This application is a continuation-in-part of patent application Ser. No. 08/558,356 filed Nov. 16, 1995, now U.S. Pat. No. 5,699,274.

STATEMENT REGARDING FEDERALLY SPONSORED RESEARCH OR DEVELOPMENT

Not Applicable

BACKGROUND OF THE INVENTION

The development of improved composite materials, particularly wood-based materials, such as plywood, oriented strand board, wafer board and the like, has led to increased use of these materials in both engineering and nonengineering applications. Despite increased demand and use, manufacturers of composite materials often suffer significant quality control problems. Wood-based composite materials can vary relatively widely in strength due to the composite nature of the products and the difficulty in achieving uniform strength in the bonding used to join the components together. Additionally, variations in the feedstocks and other factors make manufacture of uniformly strong and elastic structures from composite elements difficult and costly.

In the industries producing structural-use materials, certain performance standards and performance test methods have been promulgated by various governmental and trade organizations, e.g., the U.S. Department of Commerce and the American Society of Testing and Materials (ASTM), to insure product uniformity. A manufacturer must not only meet such product standards to qualify initially for approval of its products, but must maintain ongoing quality, i.e., must conduct a quality assurance program. To assure and maintain quality, manufacturers have an ongoing sampling program to performance test product. Typically, manufacturers must ship many samples weekly from the manufacturing site, e.g., the mill, where the products are made, to remote test centers or laboratories for performance testing. The cost of transportation and testing is significant because a manufacturer may send as many as fifty panels every week to a test site. There has been very little in the way of reliable in-house testing at the manufacturer's site.

One known test for wood-based panels is to take small samples of the panels, e.g., a 1-inch×5-inch coupon, and submit them to a universal test machine in which the sample is stressed to breaking. While such testing is quick and can be accomplished in-house, it has proved unreliable in identifying defects and has mistakenly identified usable product as defective, in the latter case, leading to a significant waste of usable product.

Various patents have attempted to respond to some of the problems of performance testing composite materials, especially wood products. For example, U.S. Pat. No. 4,589,288 issued to Porter et al. discloses a static bending apparatus for grading wood panels. U.S. Pat. No. 4,838,085 issued to Pellerin et al. discloses methods and an apparatus for non-destructive evaluation of various mechanical properties of composite materials. Other patents that disclose methods of inspection and grading of wood products include, Canadian Patent 918286; U.S. Pat. No. 4,313,348 issued to Madsen; U.S. Pat. No. 5,237,870 issued to Fry et al.; U.S. Pat. No. 3,194,063 issued to McKean; U.S. Pat. No. 3,513,690 issued to Pellerin et al.; and U.S. Pat. No. 5,423,991 issued to Collins.

Nondestructive inspection and testing of materials of all sorts are known. For example, U.S. Pat. No. 5,127,271 issued to Sato et al. describes a method of nondestructive inspection of resinous automotive bumper beams, while U.S. Pat. No. 4,982,609 issued to Talley, III discloses a test device for vehicle roof stiffness. Others have disclosed methods of performance testing of materials based on ultrasonic or acoustic techniques. See, e.g., U.S. Pat. No. 3,504,532 issued to Muenow et al.; U.S. Pat. No. 3,512,400 issued to Lynnworth; U.S. Pat. No. 3,858,437 issued to Jarzynski et al.; U.S. Pat. No. 4,201,093 issued to Logan; U.S. Pat. No. 4,338,820 issued to Jassby et al.; U.S. Pat. No. 4,481,820 issued to Thomann; and U.S. Pat. No. 4,492,117 issued to Chubachi. U.S. Pat. No. 2,439,130 issued to Firestone discloses the use of supersonic vibrational waves for inspection of materials qualities. U.S. Pat. No. 3,888,108 issued to Brands discloses a method for impact testing of pavements. U.S. Pat. No. 4,213,349 issued to Miura discloses a method of measuring stiffness of a test piece. U.S. Pat. No. 4,147,064 discloses using stress waves for determining elastic properties of a material.

Most of the known methods for performing certain standards tests are manual methods. For example, to conduct a concentrated load test, it is known to build a frame with beams simulating joists in a building construction. The beams are spaced apart depending upon the end use and span rating of the panel to be tested. A hydraulically-actuated load is applied to the panel at a specified distance from a non-secured edge and the deflection of the panel is measured by placing a dial micrometer under the panel at a position opposite the load and reading the deflection on the micrometer scale.

Despite recognition and study of various aspects of the quality assurance problems with wood-based panels, virtually all of the known methods are manual, labor intensive procedures that can readily lead to error or operator tampering. Most only permit testing of small sample specimens rather than full size panels. Accordingly, there is a significant need for methods and apparatus for performance testing of structural elements such as wood panels to provide a reliable quality assurance program for a manufacturer, a system which is fully automatic, eliminates human error and readings, is usable in-house by the manufacturer and permits testing of full size panels.

BRIEF SUMMARY OF THE INVENTION

The present invention provides a fully automatic structural-use panel performance test system which provides timely and tamper-free quality control testing. The test system is designed for use by a manufacturer on a daily basis to provide daily test results, rather than the weekly results of prior art practices. As such, the system provides reliable monitoring of product quality, heretofore totally unheralded in the prior art. The system is also very cost effective to the manufacturer. Savings are realized in the elimination of transportation and outside laboratory testing costs as well as the ability to correct quality performance problems immediately when they arise. The system in accordance with the present invention is particularly suitable for concentrated load testing, i.e., performance of a material under a load concentrated in a single area, including edge support system testing, and static bending testing. The system automatically applies a load to a panel to be tested, reads and records deflection of the panel without operator involvement, and provides a printed test report.

The foregoing, and other advantages of the present invention, are realized in one aspect thereof in a panel performance testing system which includes a support frame, a load-applying assembly, a linear measurement sensor, and a computer. The support frame supports and, depending on the particular test, clamps a panel to be tested. The panel is dimensioned as a flat, rectangular piece with two major and opposite surfaces. The frame includes (i) a horizontal support section and (ii) a clamping assembly which is supported on the horizontal section. The clamping assembly supports one major surface (i.e., under surface) of the panel along three spaced apart parallel framing members extending substantially across the width of the panel and capable of bearing against the other major surface (i.e., upper surface) of the panel along the same three spaced apart parallel framing members extending substantially across the width of the panel.

The load-applying assembly is supported on the support frame, for applying a substantially linear load to the other surface (i.e., upper surface) of the panel. The assembly includes a load cell for developing and transmitting a load-indicating signal corresponding to the applied load. The load is suitably applied via an hydraulically actuated system.

The linear measurement sensor measures the magnitude of deflection of the panel under the applied load. The sensor is suitably a linear displacement transducer for developing and transmitting a deflection-indicating signal corresponding to the deflection of the panel under the applied load.

The computer is operatively connected to the load cell and the transducer, and is configured to receive and process the load-indicating signal and the deflection-indication signal into data records of measured loads and measured deflections to determine, e.g., in one test, whether a measured deflection is greater than a predetermined standard, i.e., maximum permitted, deflection. The computer also automatically applies the load to the panel.

The clamping assembly includes three substantially C-shaped clamps. Each of the clamps has a bottom framing member for supporting the one major surface of the panel and a top portion for clamping against the other major surface of the panel. The top portion of each clamp includes a bottom surface, a first plate beneath the bottom surface, a second plate beneath the first plate and a hose sandwiched between the first plate and bottom surface. The hose is operatively connected to a pneumatic system for admitting and exhausting air to and from the hose. A second plate abuts and is coextensive with the first plate, and is substantially T-shape. The second T-plate has a flat, substantially rectangular top member and a perpendicular member downwardly depending lengthwise from the top member. The downwardly depending member has a plurality of protruding, linearly aligned and spaced apart pins. In use, the pins hold fast the panel, simulating nails fastening a panel to joists.

To accommodate a full size 4 ft×8 ft panel and to perform edge support system testing, the system in accordance with the present invention further includes extensions to each C-shaped clamp. Such extensions include a bottom extension to each of the bottom framing member of each clamp and an top extension to the top portion of each clamp. Each top extension is constructed similar to the top portion of each clamp, with a separate hose connected to the pneumatic system of the present invention.

In another aspect, the invention is a load and deflection-measuring system. The system includes a hydraulic subsystem for applying a load to a wood panel to be tested; a load cell, operatively associated with the hydraulic subsystem, for measuring the applied load; a linear displacement transducer for measuring a linear displacement of the panel under the applied load; and a computer for storing and executing a load/deflection measuring program and having a display and at least one user input device. The computer is operatively coupled to the hydraulic subsystem, for controlling the application of the load, and operatively coupled to the load cell and the transducer for recording and processing data relating to the applied load and the deflection. The computer is of the type having a central processing unit, a memory medium and data storage means for storing data records.

The load/deflection measuring program is executed on the computer, for controlling a load/deflection test. As such, the program operatively communicates with the central processing unit, memory and data storage means, for controlling the applied load, receiving a load-indicating signal from the load cell, receiving a deflection-indicating signal from the transducer, processing the deflection-indicating signal into a measured deflection value, and, in one test, comparing the measured displacement value with a standard value, and determining if the measured deflection is greater than the standard value.

In a further aspect, the invention provides a method of testing the performance of wood panel under a concentrated load, said method comprising the computer-assisted steps of (a) storing, in a data table, predetermined standard load and deflection parameters corresponding to end use and span rating of panels, (b) entering end use and span rating data for a panel to be tested, (c) determining a predetermined load for a panel to be tested depending upon the end use and span rating of the panel, and (d) testing the performance of the panel upon application of the load. The testing step includes (i) applying the load to the panel clamped to support surfaces at predetermined span intervals depending upon the span rating of the panel, (ii) measuring the load and developing a load-indicating signal corresponding to the applied load; (iii) measuring the deflection of the panel upon application of the load and developing a deflection-indicating signal corresponding to the measured deflection; (iv) interpreting the load-indicating signal and the deflection-indicating signal to derive measured test data of load and deflection, (v) analyzing the measured test data and a predetermined standard deflection parameter to determine whether the measured deflection of the panel is greater than the standard deflection; (vi) providing a test result; and (vii) printing a report of the test result.

In yet another aspect, the invention is an apparatus for measuring deflection of a material composed of a wood-based panel under application of a predetermined standard load. The apparatus includes first, second and third supports for supporting a panel at spaced apart finite locations, and a load-applying assembly for imparting a load to the panel midway between the supports. The assembly includes a loading disk and an hydraulic means for applying force to the loading disk. The apparatus also includes a load cell operatively connected to the loading disk for measuring the load applied through the loading disk and imparted to the panel, and a transducer operatively connected to the load-applying assembly for measuring the deflection sustained by the panel as a result of the imparted load.

The apparatus further includes a computer for storing and executing a load/deflection measuring program and having a display and at least one user input device, and operatively coupled to the load-applying assembly, the load cell and the transducer. The program records and processes measured data relating to the imparted load and the deflection and, in a concentrated load test, compares the measured data to standard maximum data to determine if the measured data exceed the standard maximum data. The program also includes printing a report of test results and a graphical representation of applied load versus measured deflection.

In still another aspect, the invention is a method for testing the strength performance of edge support systems, e.g., tongue-and-groove systems. The method for testing edge support systems for joining panels together includes, among other things, supporting first and second panels at first, second and third supports spaced apart at finite locations in accordance with the apparatus of the present invention. The first and second panels are joined at their edges to form an edge support joint. The panels are clamped into the clamping assembly of the present invention. The method further includes determining a predetermined standard load for the panels to be tested depending on end use and span rating; imparting the standard load to the joined panels midway between the first and second supports and proximate the edge support joint; measuring the load applied to the joined panels midway between the first and second supports and proximate the edge support join and developing a load-indicating signal corresponding to the applied load; measuring a deflection of the joined panels as a result of applying the load and developing a deflection-indicating signal corresponding the measure deflection; interpreting the load-indicating signal and the deflection-indicating signal to derive test data of applied load and measured deflection; and analyzing the measured deflection and the predetermined standard deflection to determine whether the measured deflection of the joined panels is greater than the standard deflection.

In a further aspect, the invention is a method of measuring the static bending properties of a wood-based panel, including calculating the modulus of elasticity (MOE), the modulus of rupture (MOR), the internal binding (IB) and the bending stiffness (EI) of the panel. The static bending test system includes a hydraulic subsystem for applying a continuous load to a panel to be tested up to a rupture load, a load cell, operatively associated with the hydraulic subsystem, for measuring the applied load, a linear displacement transducer for measuring a deflection of the panel under the applied load, and a computer for storing and executing a load/deflection measuring program. The computer is operatively coupled to the hydraulic subsystem, the load cell and the transducer, for recording and processing data relating to the applied load and the corresponding displacement. The load/deflection program controls the static bending test; namely, controlling the applied load; receiving displacement-indicating signals from the transducer and load-indicating signals from the load cell; receiving a rupture-indicating signal from the load cell; processing the load-indicating signals, the displacement-indicating signals and the rupture-indicating signal to derive test data of applied load, measured deflection corresponding to the applied load, and a maximum load; and using the test data to compute a measure of the bending of the panel.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWING(S)

The preferred exemplary embodiment of the present invention will hereinafter be described in conjunction with the appended drawing wherein like designations refer to like elements throughout and in which.

Figure 21:
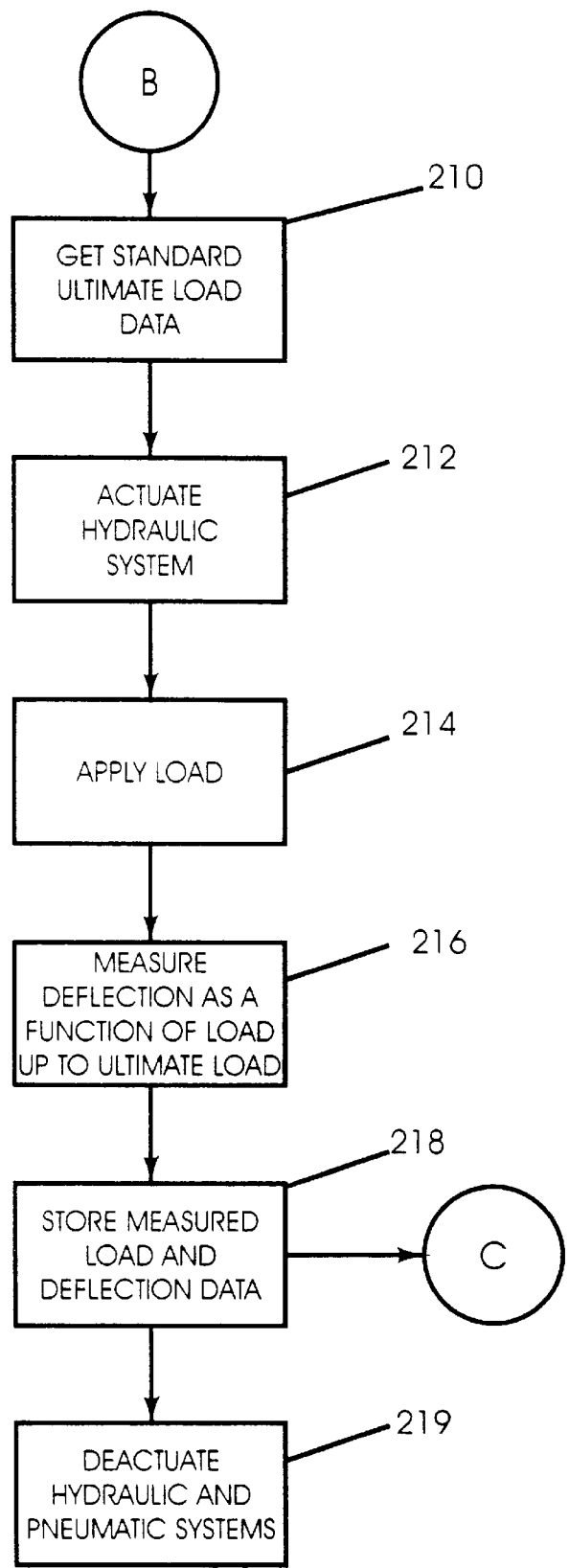
Figure 22:
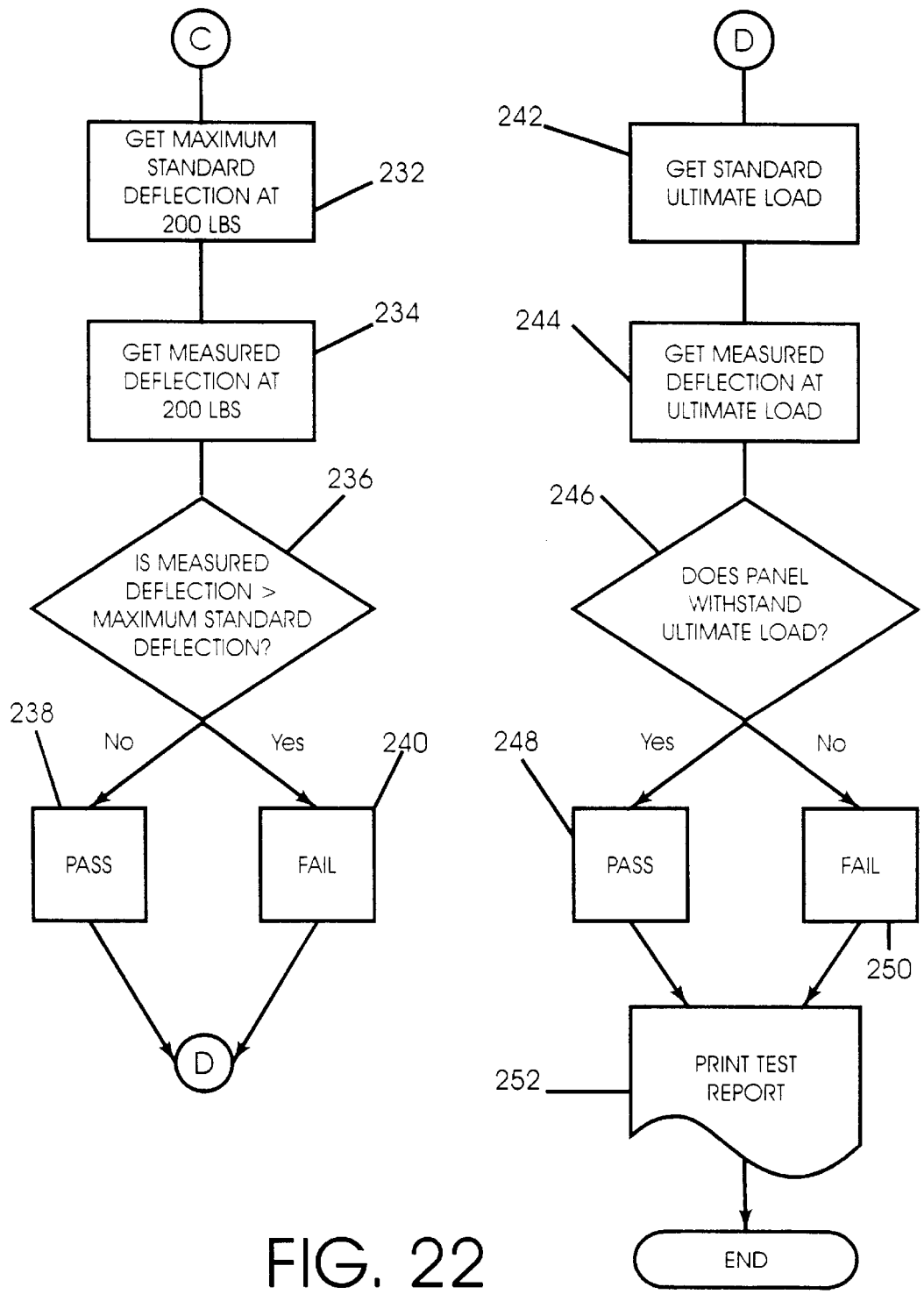
Figure 23:
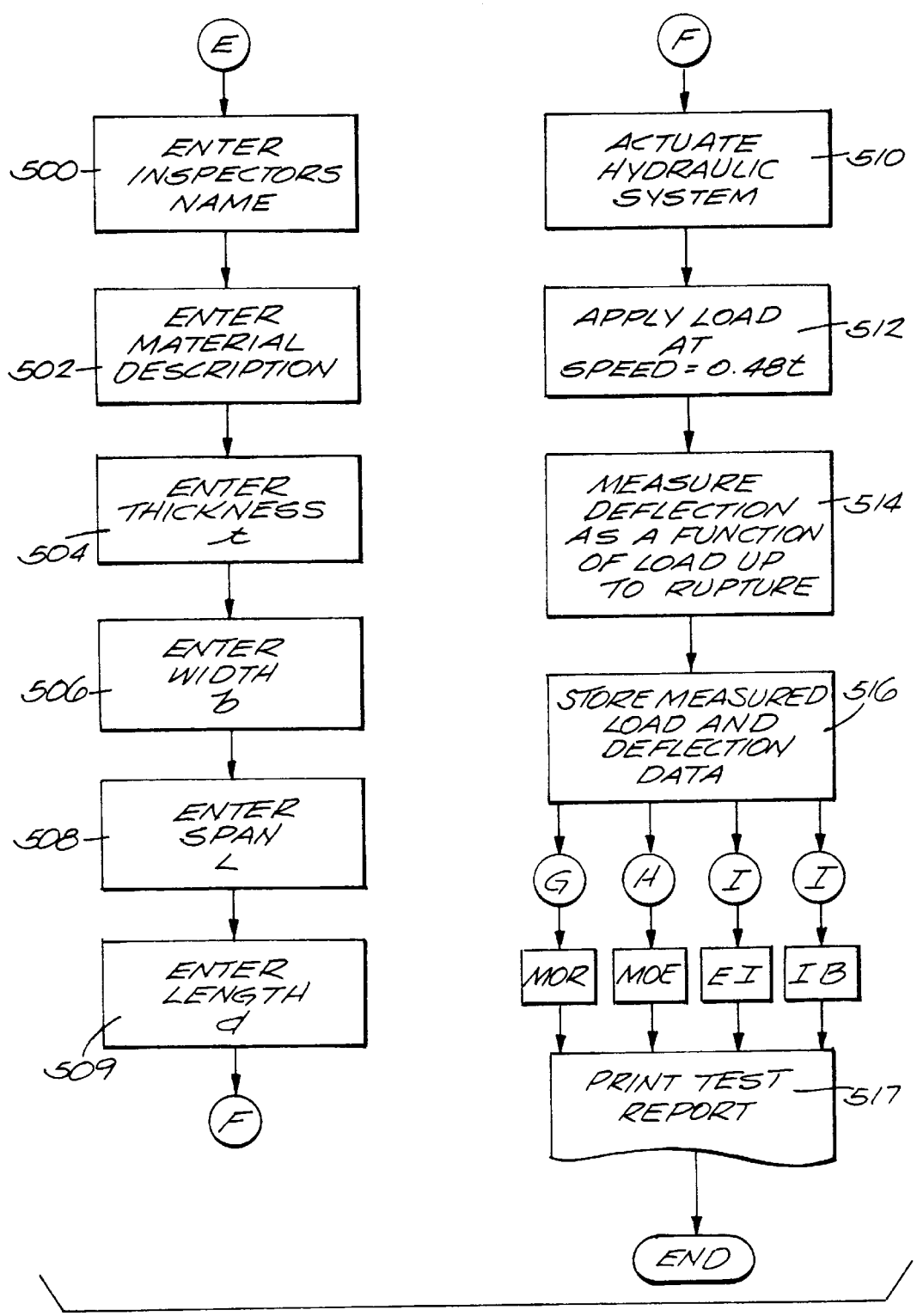
Figures 24, 25:
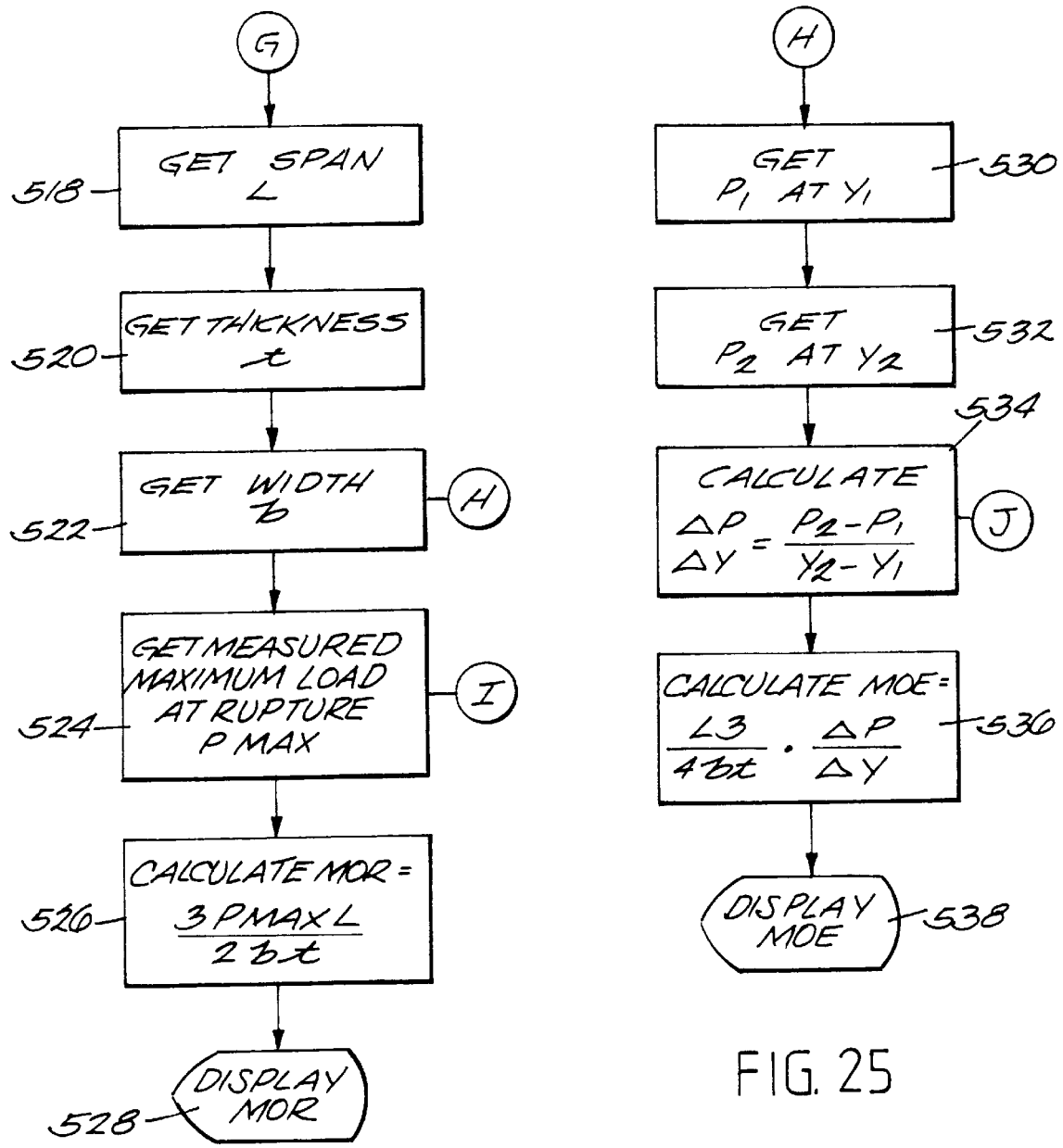
Figure 26:
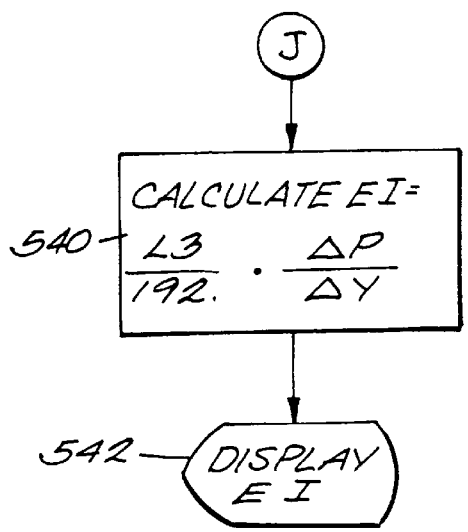
Figure 27:
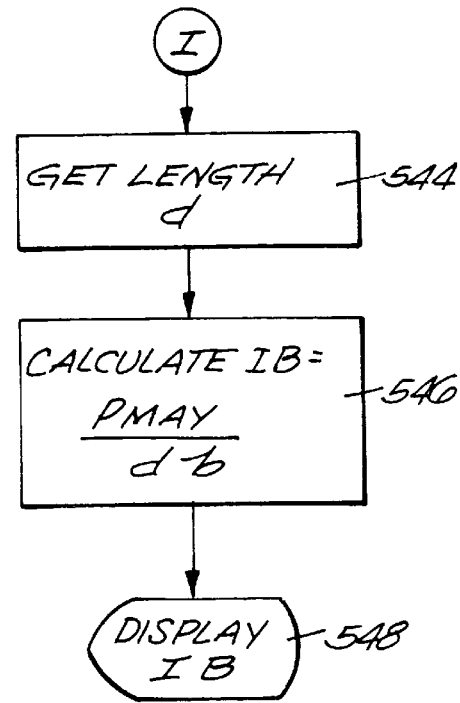
Figure 28:
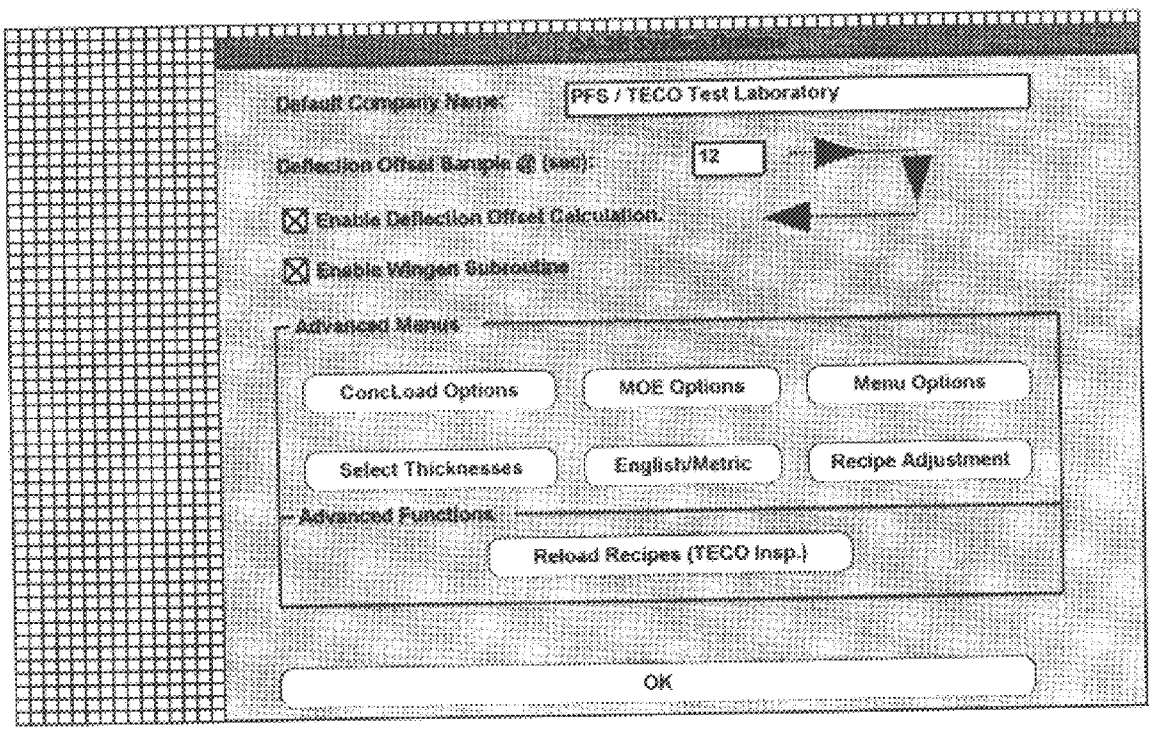

FIGS. 21 and 22, together, are flowcharts illustrating load deflection test logic of the computer program in accordance with the present invention;

FIG. 23 is a flowchart illustrating logic for MOE options of the computer program in accordance with the present invention;

FIG. 24 is a flowchart illustrating logic for the calculation of MOR for a test panel;

FIG. 25 is a flowchart illustrating logic for the calculation of MOE for a test panel;

FIG. 26 is a flowchart illustrating logic for the calculating El for a test panel;

FIG. 27 is a flowchart illustrating logic for calculating IB for a test panel;

FIG. 28 is an illustrative menu screen for test options;

Figure 29:
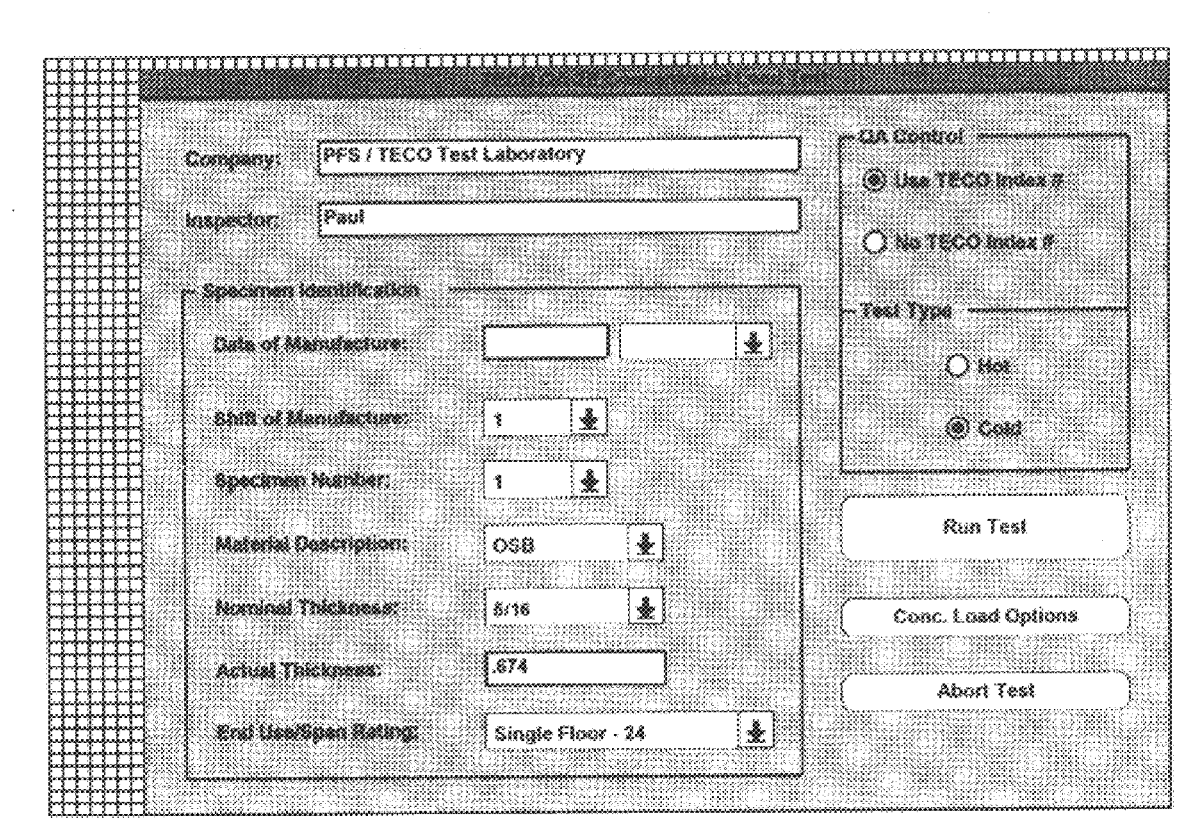

FIG. 29 is an illustrative concentrated static load test data entry screen;

Figure 30:
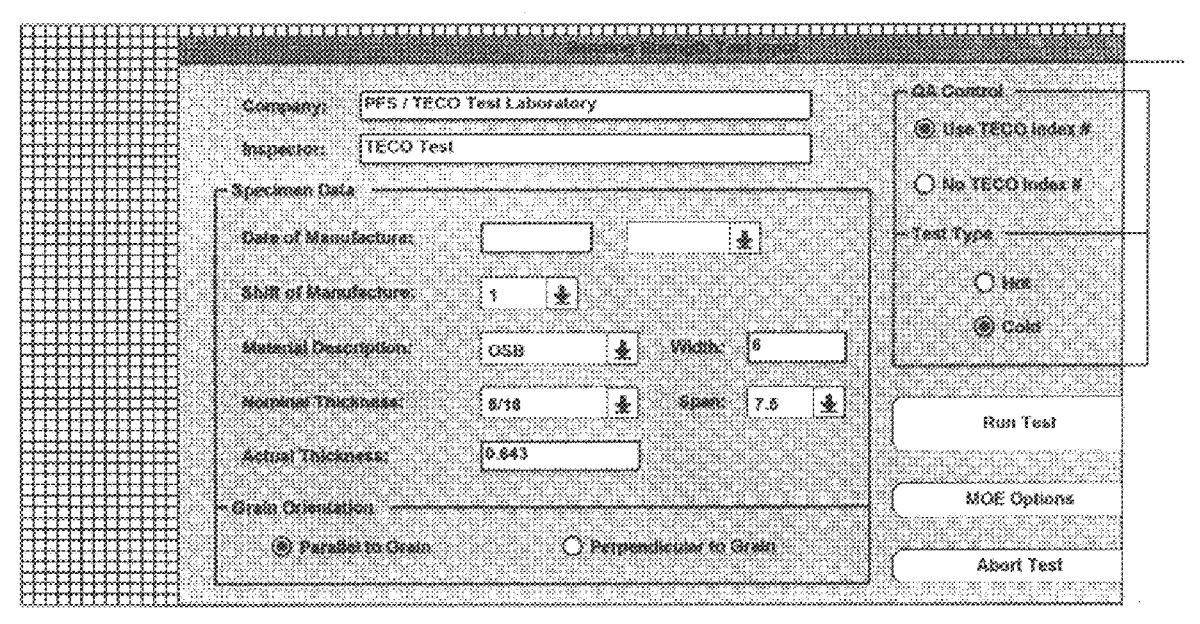

FIG. 30 is an illustrative static bending test data entry screen;

FIG. 31 is an illustrative load deflection test result report output of the computer program in accordance with the present invention; and FIG. 32 is an illustrative test report output of the computer program in accordance with the present invention wherein the panel tested failed the ultimate load test.

DETAILED DESCRIPTION OF THE INVENTION

The present invention relates to performance testing of wood-based products, for example, plywood and oriented strand board (OSB). Accordingly, the present invention will now be described in detail with respect to such endeavors; however, those skilled in the art will appreciate that such a description of the invention is meant to be exemplary only and should not be viewed as limitative on the full scope thereof.

The present invention provides a fully automatic structural-use panel performance test system which provides timely and tamper-free quality control testing. The system is designed for daily use by a manufacturer to give prompt test results for quality assurance. As such, the system provides the manufacturer the opportunity to react quickly so that necessary process control changes can be made to assure product quality. The system in accordance with the present invention is particularly suitable for concentrated load and bending strength testing. The system automatically applies a load to a panel to be tested, reads and records deflection or bending of the panel without operator involvement, and provides a printed test report. These attributes are achieved through a novel combination of structural components and physical features.

In the following description of the method of the invention, process steps are carried out at room temperature and atmospheric pressure unless otherwise specified. As used herein, the term "panel" refers to any structural-use material, particularly composite materials such as wood-based panels, e.g., oriented strand board and plywood.

Reference is initially made to FIGS. 1–15 depicting an exemplary performance/quality assurance test apparatus, generally designated as reference numeral 20, in accordance with the present invention. Specifically depicted is an apparatus for testing load deflection and/or static bending for a panel 21, especially a wood-based panel such as oriented strand board (OSB) or plywood. Such panels are typically manufactured in the form of a flat, rectangular piece, i.e., a large sheet, which may be two to four feet in width and four to eight feet in length. Thicknesses range from about 0.25 inch to 1.5 inches. As such, panel 21 has a first major surface 23 and a second opposite major surface 25.

Figure 1:
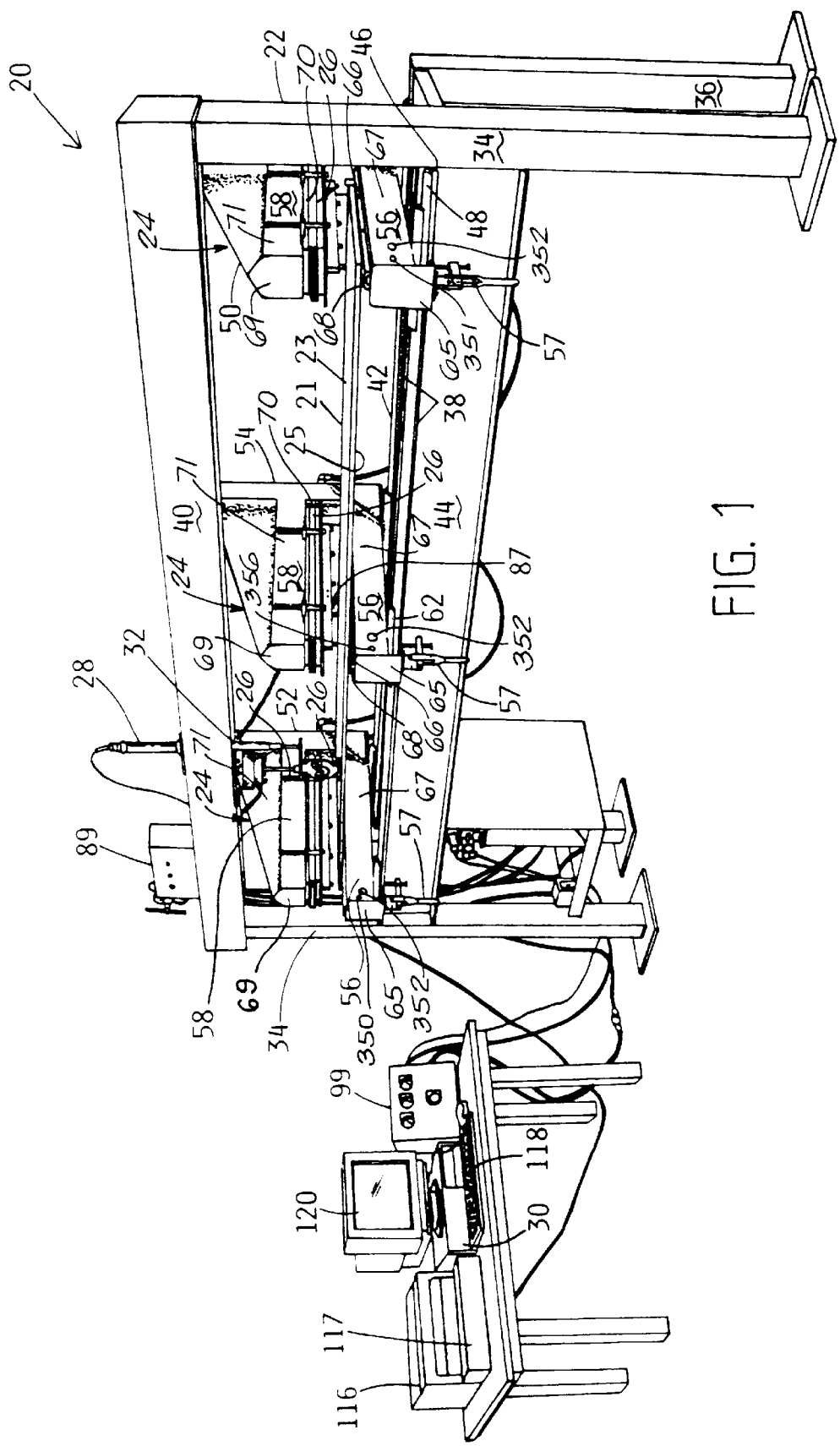
FIG. 1 is a perspective view of an exemplary system constructed in accordance with the present invention, illustrating the system without clamp extensions.

As seen in FIG. 1, apparatus 20 includes a support frame 22, a clamping assembly 24, a load-applying assembly 26, a linear displacement sensor 28, and a computer 30. Frame 22 supports the wood panel to be tested, the assemblies 24 and 26, and linear displacement sensor 28. The clamping assembly 24 holds the panel 21 fast, and as described in detail hereinafter, simulates the nailing of the panel onto a joist. The load-applying assembly 26 is hydraulically actuated and applies a concentrated load to the panel. The linear displacement sensor 28 is in the form of a linear displacement transducer 32 which measures the deflection of the panel sustained under the load.

Figure 4:
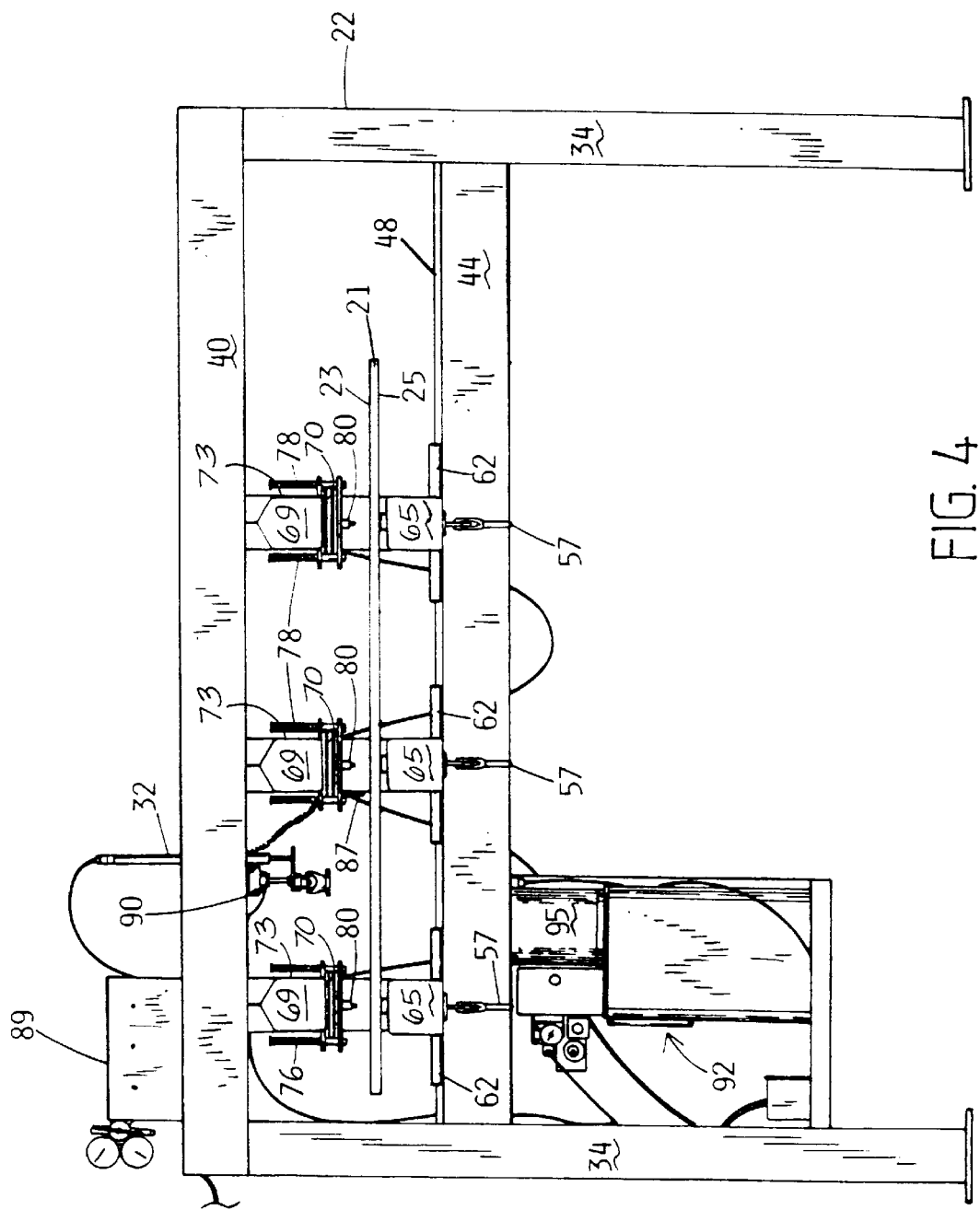
FIG. 4 is a partial front elevational view of the system of FIG. 1 shown supporting of a panel to be tested.
Figure 5:
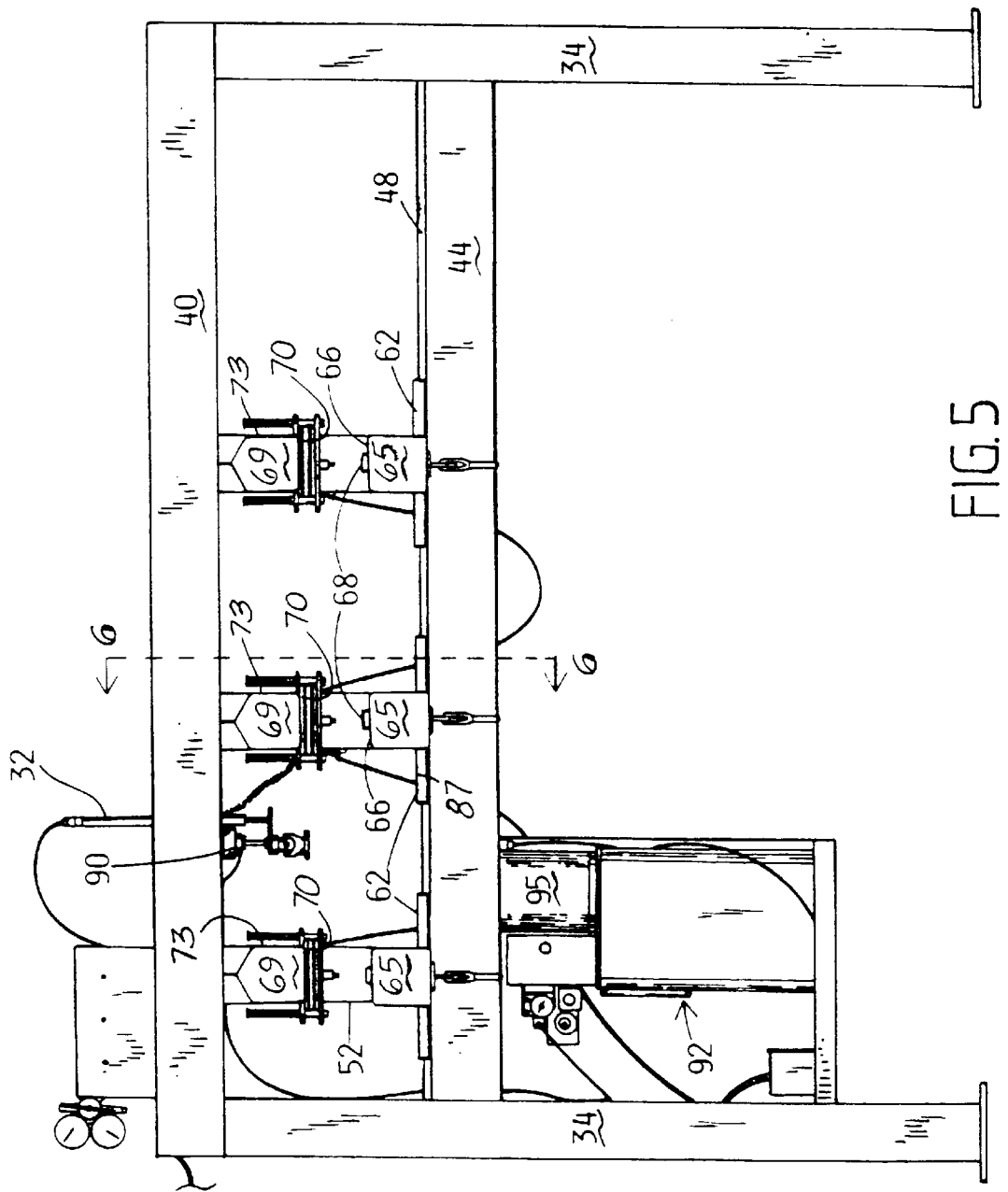
FIG. 5 is a partial front elevational view of the system of FIG. 1 shown without supporting a panel to be tested.

As best seen in FIGS. 4 and 5, the support frame 22 includes a pair of upright, spaced apart front posts or front columns 34, a pair of upright, spaced apart rear posts 36 which are about half the length of front posts 34, a horizontal support section 38 and a cross beam 40 connecting the top ends of upright posts 34. Horizontal support section 38 includes two parallel spaced apart beams 42 and 44. Beam 42 connects the top ends of rear posts 36 and is supported thereby; beam 44 is affixed substantially at the midpoints of front posts 34. The horizontal support section 38 is of sufficient width and length to accommodate panel 21, typically a width of 24 inches. Posts 34 and 36 and cross beam 40 are suitably structural steel posts, and parallel beams 42 and 44 are suitably structural steel I-beams. In overall dimension, the frame 22 is suitably about 9 ft in length and about 3 ft. in width.

Figure 9:
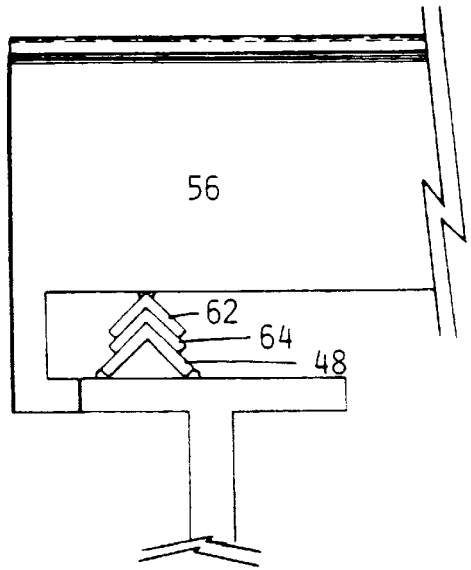
FIG. 9 is an enlarged side view of one of the rails upon which the clamping assembly slides in accordance with the present invention.

Each parallel beams 42 and 44 has a top side 46, e.g., a top of the I-beam, to which is mounted an elongate rail 48 which extends the length of each beam, i.e., rails 48 are parallel and spaced apart as are beams 42 and 44. As best seen in FIG. 9, rails 48 are in the shape of an angled section, i.e., when viewed on end, is an inverted V-shape.

Figure 6:
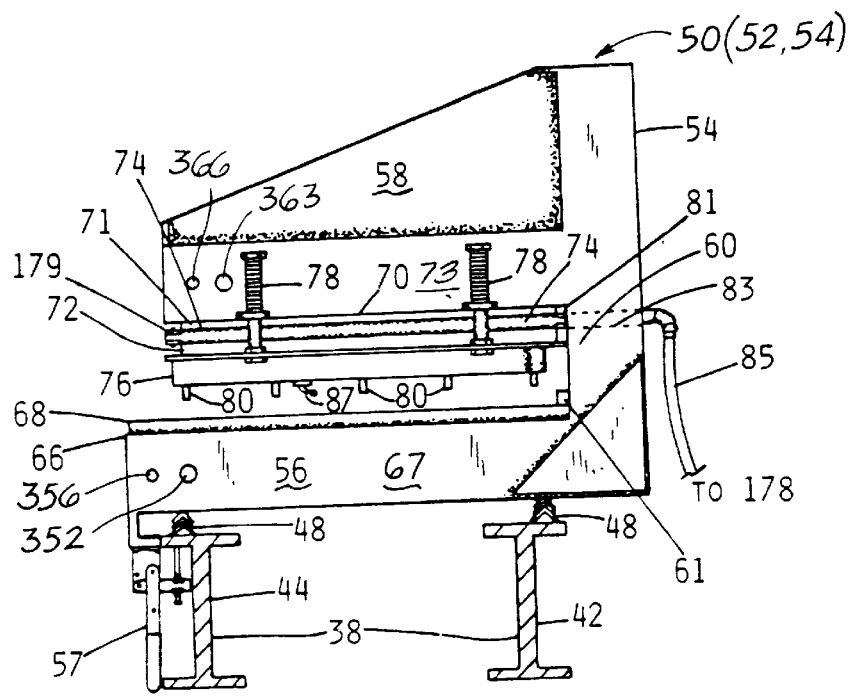
FIG. 6 is a partial side elevational view of a clamp of the clamping assembly illustrated in FIG. 1 taken along line 6–6' of FIG. 5.
Figure 7:
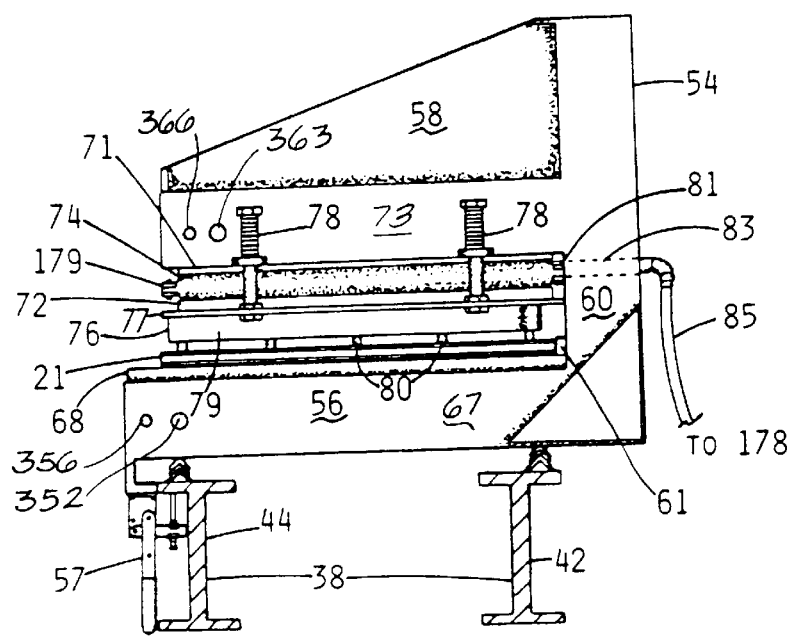
FIG. 7 is a partial side elevational view of the clamp of the clamping assembly illustrated in FIG. 6, with the clamp supporting and clamping a panel to be tested.

The clamping assembly 24 includes three, substantially C-shaped clamps 50, 52, and 54, respectively. As best seen in FIGS. 6 and 7, each clamp member 50, 52 and 54 has an elongate, horizontal bottom receiver framing member or receiver jig 56, an elongate horizontal top portion 58 and an upright portion 60 connecting the bottom and top members at one end, thus, forming a substantial C-shape, and suitably made of steel tubing. Receiver jigs 56 support the panel to be tested and include proximate portion 60, a panel stop 61, against which a back edge (i.e., minor edge) of panel 21 rests. Jigs 56 are movably mounted on rails 48 which extend longitudinally beams 42 and 44, and can be clamped to beam 44 via jig clamps 57. Each jig 56 has inverted V-shaped portions 62 which are complementary in shape to each rail 48. Each inverted V-shaped portion 62 has a coextensive pad 64 made of a nonstick polymeric material, e.g., Teflon™. Thus, clamps 50, 52 and 54 suitably slide along rails 48 and can be adjusted to predetermined spaced apart positions from each other.

Each jig 56 further has a front face 65, side faces 67 and a top face 66 upon which a support 68 is affixed. Support 68 is substantially in the form of an elongate inverted U-shape. In performance testing wood panels, support 68 is substantially rectangular in shape with a width of about 1.5 inches, simulating a joist. Panel 21 is supported on the three supports 68 of jigs 56.

Each top portion 58 of each clamp member 50, 52 and 54 has a front face 69, side faces 73 and a bottom face 70. Beneath and coextensive to face 70 is a first movable plate 72 and a hose 74 sandwiched therebetween. A substantially T-shaped plate 76 abuts against plate 72, and plates 72 and 76 and hose 74 are held against face 70 via a plurality of springs 78, connecting plate 76 to face 70. T-plate 76 has a flat, substantially rectangular top member 77 and a downwardly depending perpendicular member 79 running the length of T-plate 76. Member 79 has downwardly protruding cylindrical pins 80, linearly spaced apart along the length of member 77. These cylindrical pins 80 when pressed against panel 21 simulate fasteners, e.g., nails, that would be in place in actual environmental use of the panel. Preferably, the cylindrical pins 80 are 6 in. on-center pins that simulate 8-penny nail heads. Hose 74 is clamped at one end by a clamp 79 and connected at the other end with a tubing 81 through a port 83 in the back of top portion 58, via a line 85 to a pneumatic system 78, i.e., to a source of pressurized air (not shown), in a manner well-known in the art. The air pressure is regulated by an air pressure regulator as is well-known in the art. Such a regulator is shown as reference numeral 89 in FIGS. 1 and 3. Hose 74 can be inflated and deflated by admitting and exhausting pressurized air into hose 74 schematically shown in FIG. 6. It is noted that an additional plate 71, positioned directly beneath face 70 is optional depending on the thickness of the panel being tested.

As best seen in FIGS. 6 and 7, when hose 74 is inflated, T-plate 76 moves downward and pins 80 press and hold panel 21. A microswitch 87 controls the penetration of pins 80 into panel 21 to ⅛ inch. Microswitch 87 is suitably a well-known roller type actuator, e.g., Stock No. 6X285 available from Grainger of Madison, Wis. Microswitch 87 is positioned on middle clamp 52 and extends somewhat below T-plate 76 and is operatively connected to the air regulator 89. When microswitch 87 is tripped, i.e., when the roller or wheel of microswitch 87 touches panel 21, the switch closes the air flow to the hose 74 in a well-known manner. Hose 74 is suitably a 2.5-inch diameter firehose, e.g., hose #1P957 from Grainger of Madison, Wis.

Figure 2:
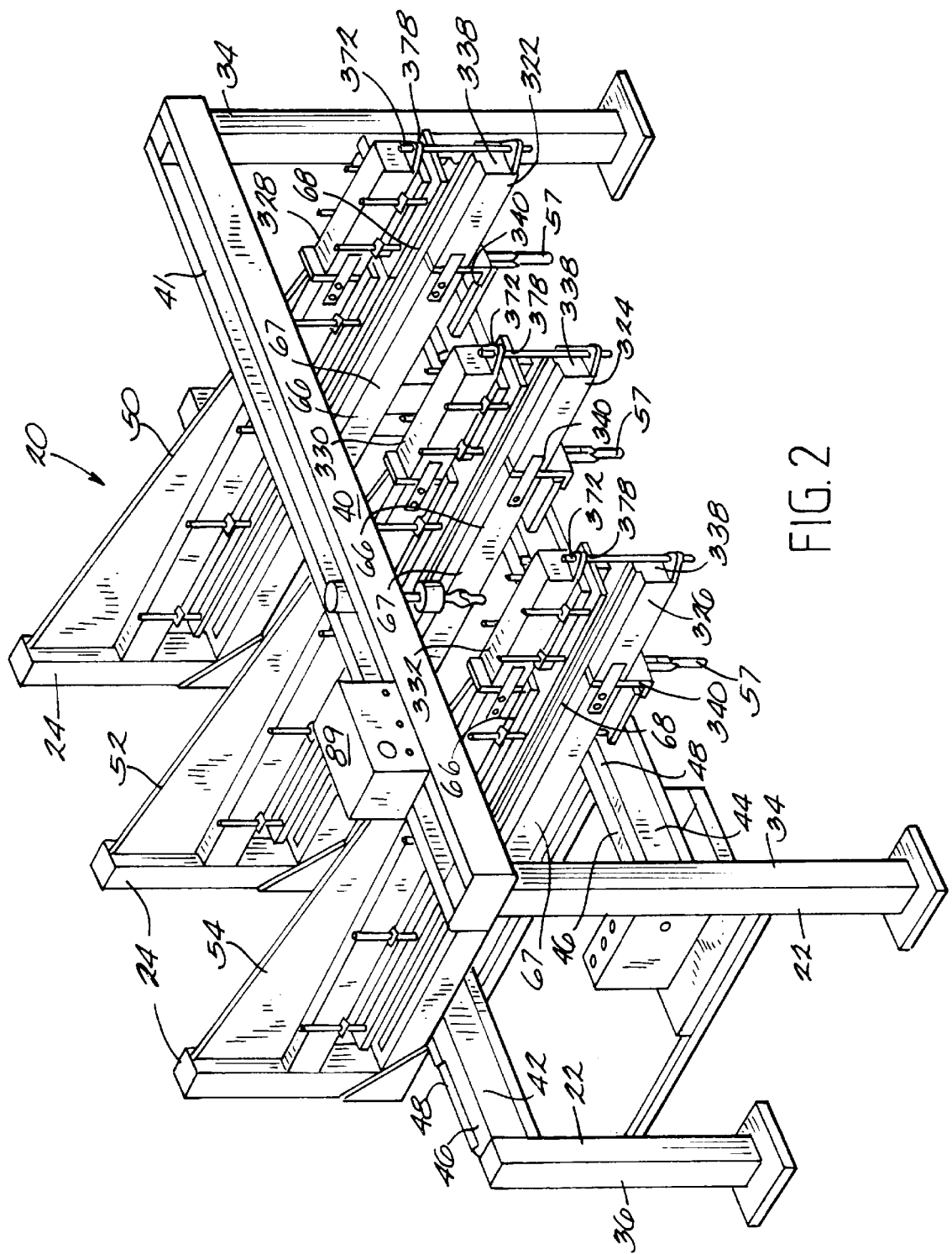
FIG. 2 is a perspective view of the system of FIG. 1, illustrating clamp extensions.
Figure 3:
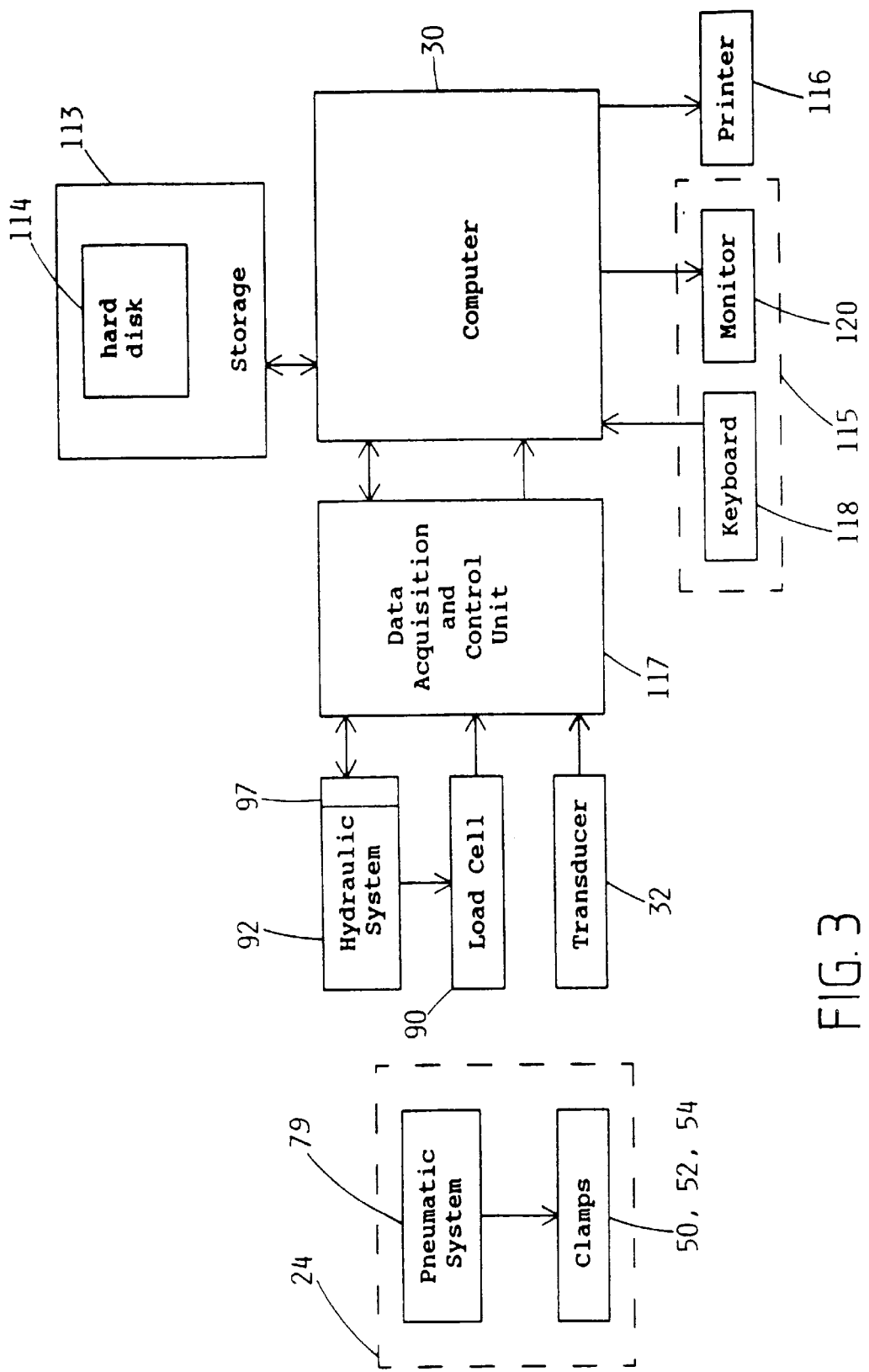
FIG. 3 is a block diagram of the hardware suitable for the exemplary system of the invention shown in FIGS. 1 and 2.
Figure 8:
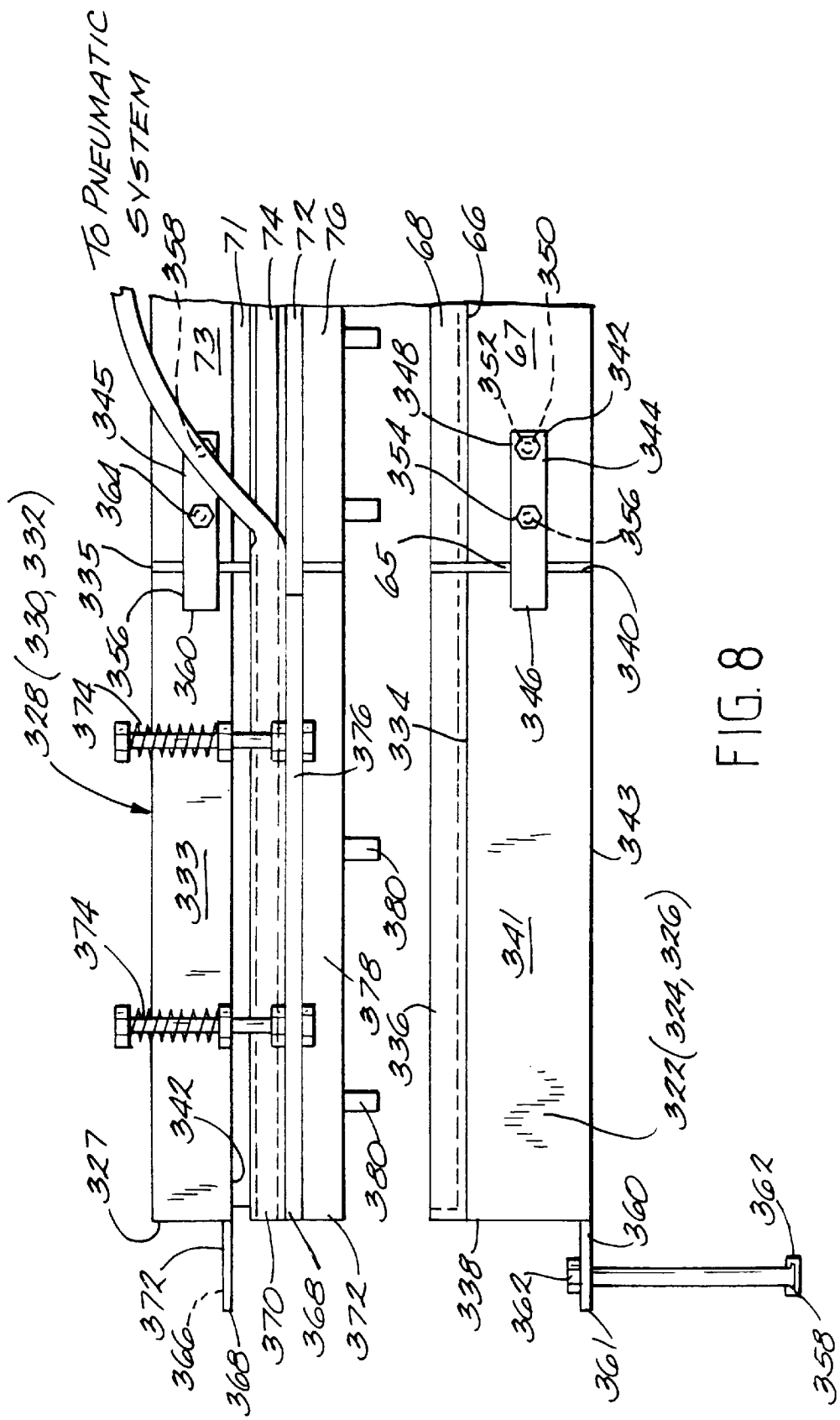
FIG. 8 is a partial side elevational view of the clamp of the clamping assembly illustrated in FIGS. 5 and 6, with the clamp extensions in place.

As best seen in FIGS. 2 and 8, apparatus 20 is suitably fitted with extensions to clamps 50, 52 and 54; namely, jig extensions 322, 324, 326, and top portion extensions 328, 330 and 332 to clamps 50, 52 and 54, respectively, so that an entire 4×8-foot panel can be tested. Jig extension 322 is attached to receiver jig 56 of C-shaped clamp 50, while jig extensions 324 and 326 are attached to jig 56 of clamp 52 and 54, respectively. Jig extensions 322, 324 and 325 are identical, and each has a top 334 upon which a elongate support 336 is affixed. Support 336 is substantially in the form of an elongate inverted U-shape. In performance testing, support 336 is substantially rectangular in shape with a width of about 1.5 inches, stimulating a joist, similar to support 68 as described hereinabove. Panel 21, when of a size of 4×8 ft, is fully supported on both the three supports 68 of jigs 56 and the three supports 336 of jig extensions 322, 324 and 326.

Jig extensions 322, 324 and 326 each further have a front face 338, a back face 340, side faces 341 and a bottom face 343. Top portion extensions 328, 330 and 332 each have a front face 327, a bottom face 337, side faces 333 and a back face 335. Back face 340 of jig extension 322 is fitted onto front face 65 of jig 56 of C-shaped clamp 50 via a clamp 342 onto side faces 67 of jig 56, while back faces 340 of jig extensions 324 and 326 are fitted on front faces 65 of jigs 50 of C-clamps 52 and 54, respectively, via clamps 342 onto side faces 67. Similarly, back faces 335 of top portion extensions 328, 330 and 332, respectively, are fitted onto front face 69 of top portions 58 of C-clamps 50, 52 and 54, respectively, via a clamp 345 to side faces 73 of top portion 58.

Each clamp 342 includes a pair of lock bars 344 each with opposed ends 346 and 348, respectively. Ends 346 are affixed to side faces 341 by conventional fastening means such as welding or bolting. Ends 348 have a slot 350 which receives a collared bolt head 352 on side faces 67 of jigs 56. Spaced apart from slot 350 is a collared bolt 354 which when bolt head 352 is received in slot 350 aligns with a hole 356 on side face 67 of jig 56. To attach a jig extension, bolt head 352 is received in slot 350 and bolt 354 is threaded into hole 352 until the jig extension is held fast and secure. Both locks bars 344 are fastened in this manner.

Similarly, clamp 345 includes a pair of lock bars 356 each with opposed ends 360 and 361, respectively. Ends 360 are affixed one to each of side faces 333 of top portion extensions 328, 330 and 332, respectively. Ends 361 each have an end slot 358. Slot 358 can receive a collared bolt head 363 affixed on side face 71 of top portion 58. Spaced apart from slot 358 is a collared bolt 364 which when bolt head 363 is received into slot 358 aligns with a hole 366 in side face 71, bolt 364 is threadedly attached to hold the extension secure.

Beneath and coextensive to bottom face 337 is a first movable plate 368 and a hose 370 sandwiched therebetween. A substantially T-shaped plate 372 abuts against plate 368, and plates 368 and 372 and hose 370 are held against face 337 via a set of springs 374, connecting plate 372 to face 337. T-plate 372 has a flat, substantially rectangular top member 376 and a downwardly depending perpendicular member 378 running the length of T-shaped plate 372. Member 378 has downwardly protruding cylindrical pins 380, linearly spaced apart along the length of member 378. The cylindrical pins 380 are substantially identical to pins 80, and when pressed against panel 21 simulate fasteners, e.g., nails, that would be in place in actual environmental use of the panel.

Hose 370 is clamped at one end by a clamp 379 and connected at the other end with a tubing 381 via a line 385 to the pneumatic system 79. Hose 370 is similarly inflated as described hereinabove for hose 74 and controlled by microswitch 87. T-plate 372 moves downward and pins 380 press and hold panel 21 in synchrony with the movement of T-plate 76 and pins 80.

Jig extensions 322, 324 and 326 each have a panel 360 affixed to and extending horizontally from bottom face 343, out from front face 338. Each panel 360 has a centrally disposed circular hole 361 through which a rod 358 with opposed ends 362 and 364 which are substantially cylindrical in shape and have diameters greater than hole 361. Top portion extensions 328, 330 and 332 each also have a panel 366 extending horizontally from bottom face 342, out from face 327. Each panel 366 has a front 368. Centrally to front 368 is a slot 372 extending from front 368 to substantially the center of panel 366. Slot 372 terminates substantially in a circular hole 374. The width of slot 372 and hole 374 is substantially the diameter of rod 358. In operation, when jig extensions 322, 324 and 326 have been clamped onto jigs 56 and top portion extensions 328, 330 and 332 have been clamped onto top portions 58, rod 358 for each jig extension is pulled up and set into hole 374 of panel 366, thus connecting each top portion extension to its bottom jig extension.

Figure 10:
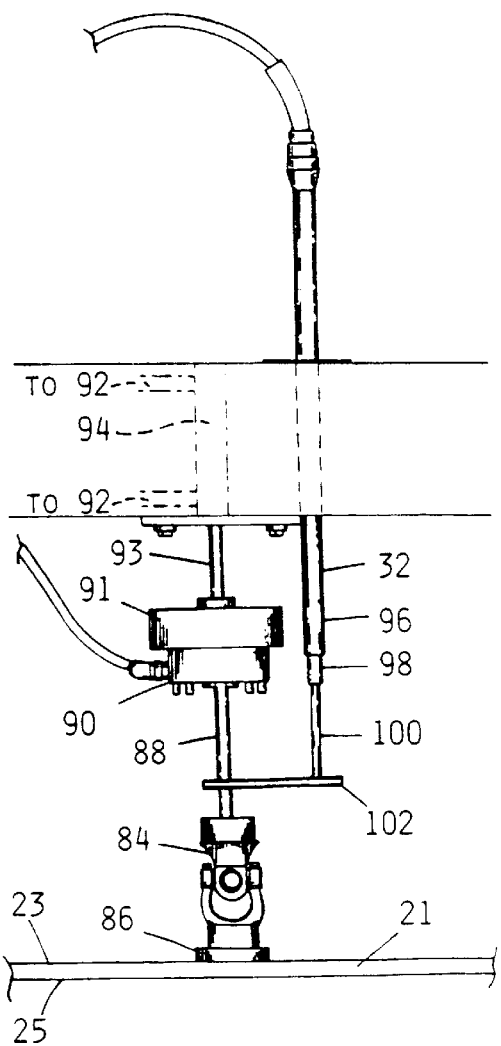
FIG. 10 is a front view of the load-applying assembly and linear displacement transducer suitable for use in accordance with the present invention.

As best seen in FIG. 10, the load-applying assembly 26 includes a universal joint 84 fitted with a flat plate or loading disk 86, and a rod 88 connected to a load cell 90. Load cell 90 is mounted on a load cell plate 91 to which is applied a load which is suitably provided by an hydraulic system 92, in a manner well-known in the art, for example, an hydraulic ram 93 connected to an hydraulic cylinder 94 which in turn is connected to an hydraulic pump 95. The load is applied via loading disk 86 to panel 21, i.e., by controlling actuation of pump 95 through hydraulic cylinder 94 to ram 93. A load cell measures the applied load in a manner well-known in the art. A load cell such as the one described herein is commercially available from Interface, Inc. of Scottsdale, Arizona, e.g., Model No. 1210AF. Pump 95 is operatively connected to computer 30 via a proportional relief valve 97, e.g., an electro-hydraulic proportional pilot relief valve available as Model No. EPR-G01-2 from Nachi America to control actuation thereof. It is noted that a manual control 99 for the hydraulic system can also be included in system 20.

As also best seen in FIG. 10, the transducer 32 has an outer cylindrical case 96 fastened to a steel channel 41 inside cross beam 40. Case 96 includes a core 98. The lower end of the core 98 is threaded to accept a sensing shaft 100 which is substantially aligned on the vertical plane of symmetry. The lower end of the sensing shaft 100 contacts a measuring plate 102 which in turn connects to rod 88 of load-applying assembly 26. Such transducers are commercially available from Sensotek of Columbus, Ohio, e.g., Model DLF DC—DC Long Stroke LVDT. The operation of such transducers, abbreviated LVDT (linear variable differential-displacement transducer), is known in the art and described in *Sensors And Analyzer Handbook* by H. N. Norton, Prentice-Hall, Inc. (1982) pp. 93–96, incorporated herein by reference.

As predetermined loads are slowly applied to panel 21, the load cell 90 measures the magnitude of the load, typically in pounds applied to panel 21, while transducer 32 records the downward linear travel of the transducer measuring plate 102 corresponding to the deflection of panel 21.

In the concentrated static load test, for example, loads are typically delivered to produce deflection at a rate of 0.2 inch/min. (about 200 lbs/min.) Predetermined loads are established in accordance with the end use and span rating of the panel to be tested. For example, wood-based panels such as OSB or plywood, the end use may be roofing, subfloor and single floor panels, sometimes called sheathing. Span ratings, i.e., the distance between joists to which the panel is fastened, range from 16 inches to 60 inches. Load and deflection standards, e.g., ultimate loads (i.e., 400, 550 or 700 lb loads that the panel must withstand without breaking) and maximum deflections at 200 lbs load, are established by the United States Department of Commerce and found is in Voluntary Product Standard PS-2, which is incorporated herein by reference and available from Timberco, Inc. of Madison, Wis. Load cell 90 and transducer 32 are operatively connected via cable to computer 30 so that load and corresponding deflection are measured, i.e., a load/deflection curve is recorded for panel 21 being tested.

Figure 11:
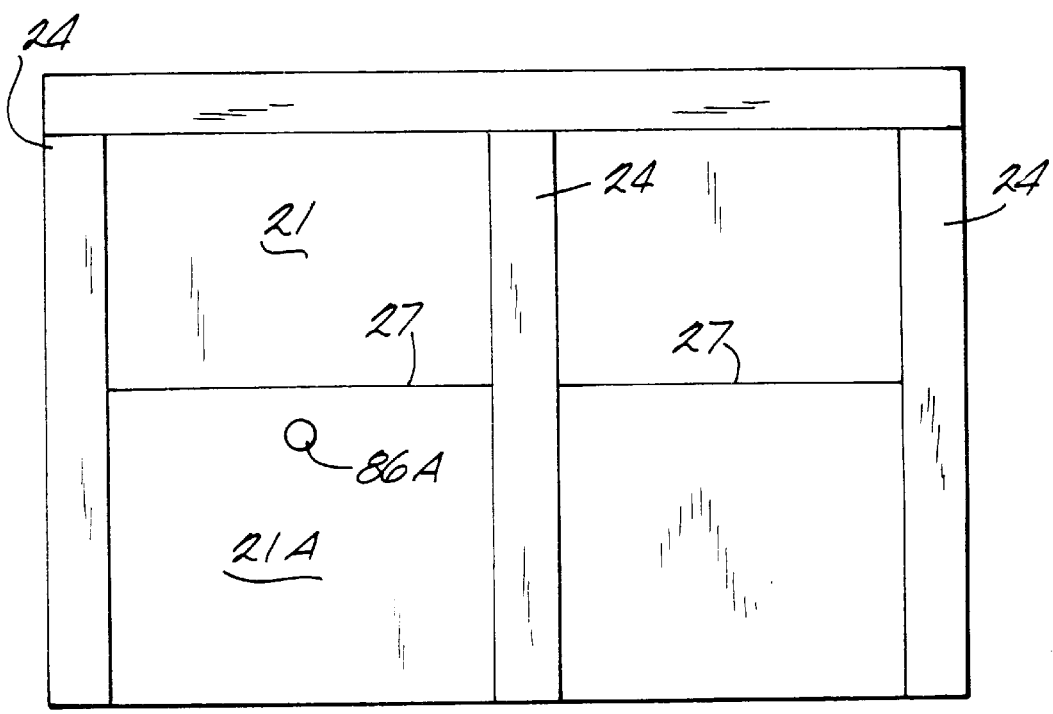
FIG. 11 is a representational top view of the application of the load in testing panels having an edge support system.
Figure 12:
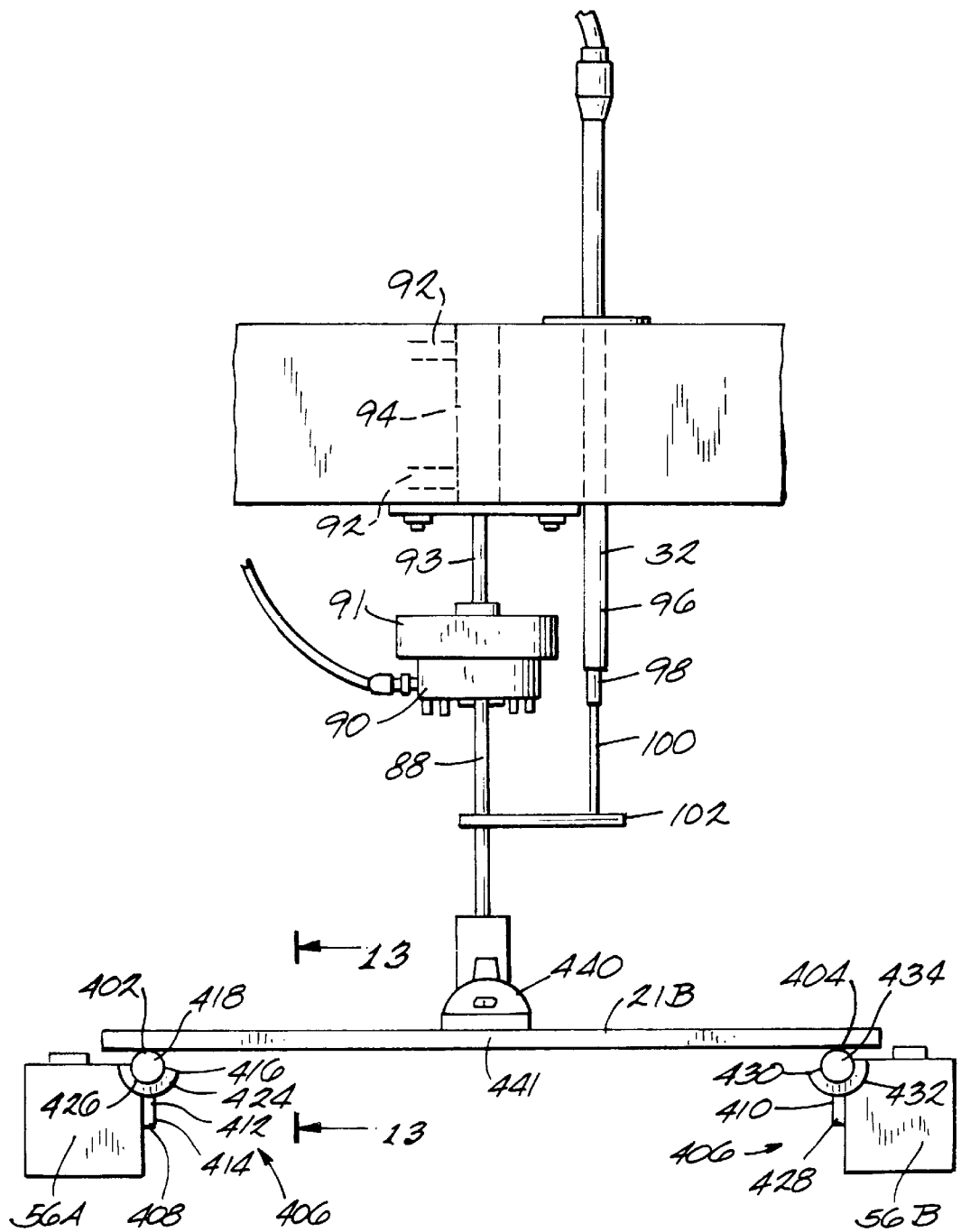
FIG. 12 is a schematic front view of the system in accordance with the present invention, illustrating the support system for the test panel for a static bending test.
Figure 13:
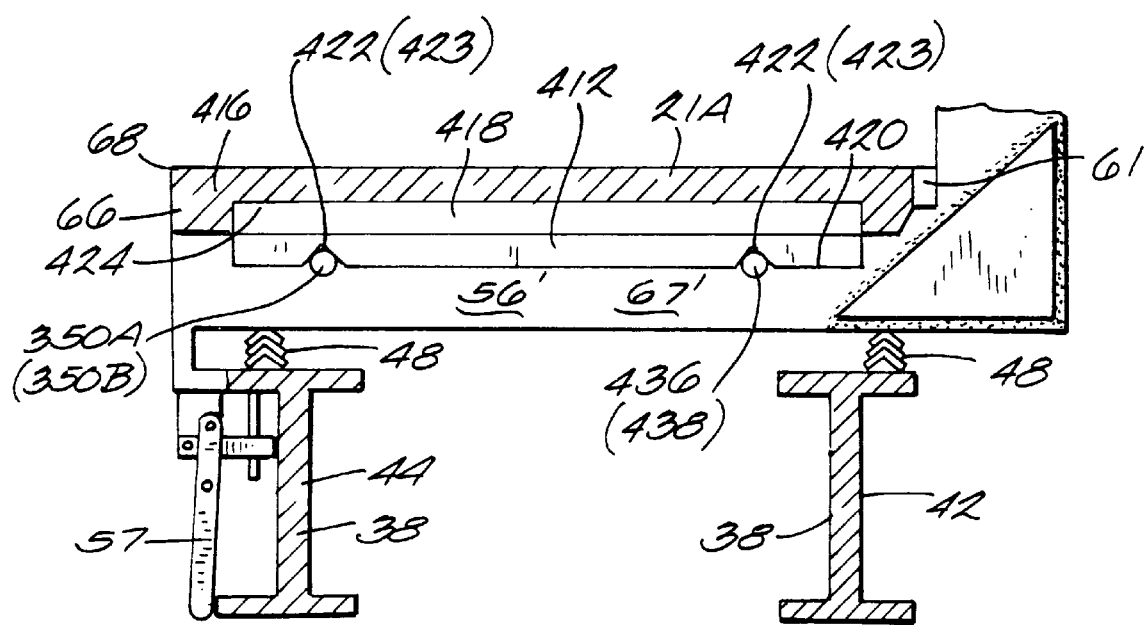
FIG. 13 is a partial side sectional view of the support system for the static bending test of a panel taken along line 13–13' of FIG. 12.

The concentrated load test can also be used to test edge support systems such as tongue-and-groove supported edge 27. To perform this test, the panel to be tested 21 has, e.g., a groove edge. The 3-in. loading disk 86 is replaced by a 1-in. loading disk 86A, and the jig and top portion extensions are installed on apparatus 20 as described hereinabove. Panel 21 is placed in clamp assembly 24, and a second panel 21A having a tongue edge is then placed in assembly 24 so that the tongue is inserted into the groove, and both panels 21 and 21A are clamped as described hereinabove. The loading disk is placed 2½ in. from the edge support system, e.g., tongue-and-groove edge support. FIG. 11 is a representational top view illustrating the placement of the loading disk for the edge support test. The ultimate load test is performed as described hereinabove.

Reference is now made to FIGS. 12–16, wherein apparatus 20 is set up for the static bending test. To test bending properties, a panel 21B is supported by its lateral edges 402 and 404 on a static bending support apparatus 406. Bending end support apparatus 406 includes a pair of rigid end supports 408 and 410, respectively. End support 408 includes an elongate, L-shaped member 412 having a first leg portion 414, a second leg portion 416 perpendicular to portion 414 and a support roller 418. Portion 414 has a bottom edge 420 which includes a pair of substantially semi-circularly notices 422. Portion 416 includes a elongate substantially semi-circular cradle 424. Cradle 424 is configured and dimensioned to hold a bottom portion 426 of support roller 418, support roller 418 being a cylindrical body. End support 410 is an L-shaped body identical to end support 408. End support 410 has a first leg portion 428 and a second perpendicular portion 430. When in position and in use, explained in detail hereinbelow, first leg portion 414 of end support 408 extends from second leg portion 416 in a direction opposite from the extension of first leg portion 428 of end support 410 from second leg portion 430. Portion 430 has a bottom edge 421 which includes a pair of substantially semi-circularly notices 423. First leg portion 428 includes an elongate cradle 432 which is identical in configuration and dimension to cradle 424. End support 410 includes a support roller 434 which is identical to support roller 418.

End support 408 is releasably attachable to jig 56A, which is one of adjacent jigs 56, on one side face 67A while end support 410 is releasably attachable to second adjacent jig 56B on the side face 67B directed toward end support 408. Side face 67A includes a first collared bolt head 350A (which is identical to bolt head 350 described hereinabove) a second collared bolt head 436, and notches 422 can receive bolt heads 350A and 436 such that second leg portion 416 is attached to side face 67A of jig 56A. Likewise, side face 67B of jig 56B includes a first collared bolt head 350B and a second collared bolt head 438, and notches 423 of leg portion 430 can receive bolt heads 350B and 438 such that second leg portion 430 is attached to side face 67B of jig 56B. When end supports 408 and 410 are so positioned on apparatus 20, wood panel 21B may thus be supported by support rollers 418 and 434 from below and across its width, at points adjacent each lateral end.

In bending test mode, loading disk 86 of load-applying assembly 26 is replaced by a loading block 440 which contacts at a mid-span 441 of a panel 21B from above, transmitting loads developed by hydraulic system 92 as described hereinbefore, across the width of panel 21B. Loading block 440 suitably includes an elongate member 442 which is substantially T-shaped, having a flat, horizontal portion 444 and a substantially perpendicular upright portion 446. Flat portion 444 is pivotally attached to upright portion 446. Portion 446 has a bottom 448 which is rounded or suitably a knife edge, lateral ends 450, longitudinal ends 452 and sides 453. Portion 444 has upright ends 452, each with a slot 454. Rocker pins 456 are attached to portion 446, each through slot 454 to each end 450 of portion 446. Rocker pin 456 is of sufficient strength to just carry flat portion 444 when not loaded.

Figure 16:
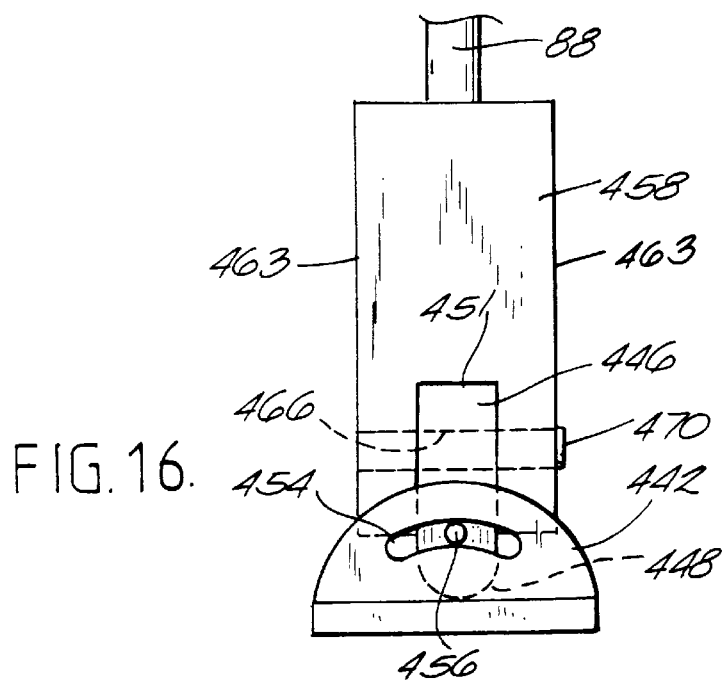
FIG. 16 is a front end view of the loading bar of FIG. 15.

Loading block 440 is suitably attached to rod 88 with a fastener member 458. Member 458 suitably has a bottom 460, opposite sides 461, opposite sides 463 and top 465. Bottom 460 has a centrally disposed cut out or trough-like portion 462 through sides 461, which portion closely receives longitudinal end 451 of portion 446. Each side 463 has a bottom 464 which ends below bottom 460, and has a centrally disposed hole 466. As seen in FIG. 16, portion 446 has a centrally disposed hole 468 in register such that a pin 470 extends therethrough. Pin 470 is sufficiently strong to withstand a 2,000 lb. shear, suitably a cylindrical pin of about ½ in. diameter.

Top 465 of member 458 has a centrally disposed hole 472 through which the lower end of rod 88 is suitably threadedly attached to member 458.

Figure 14:
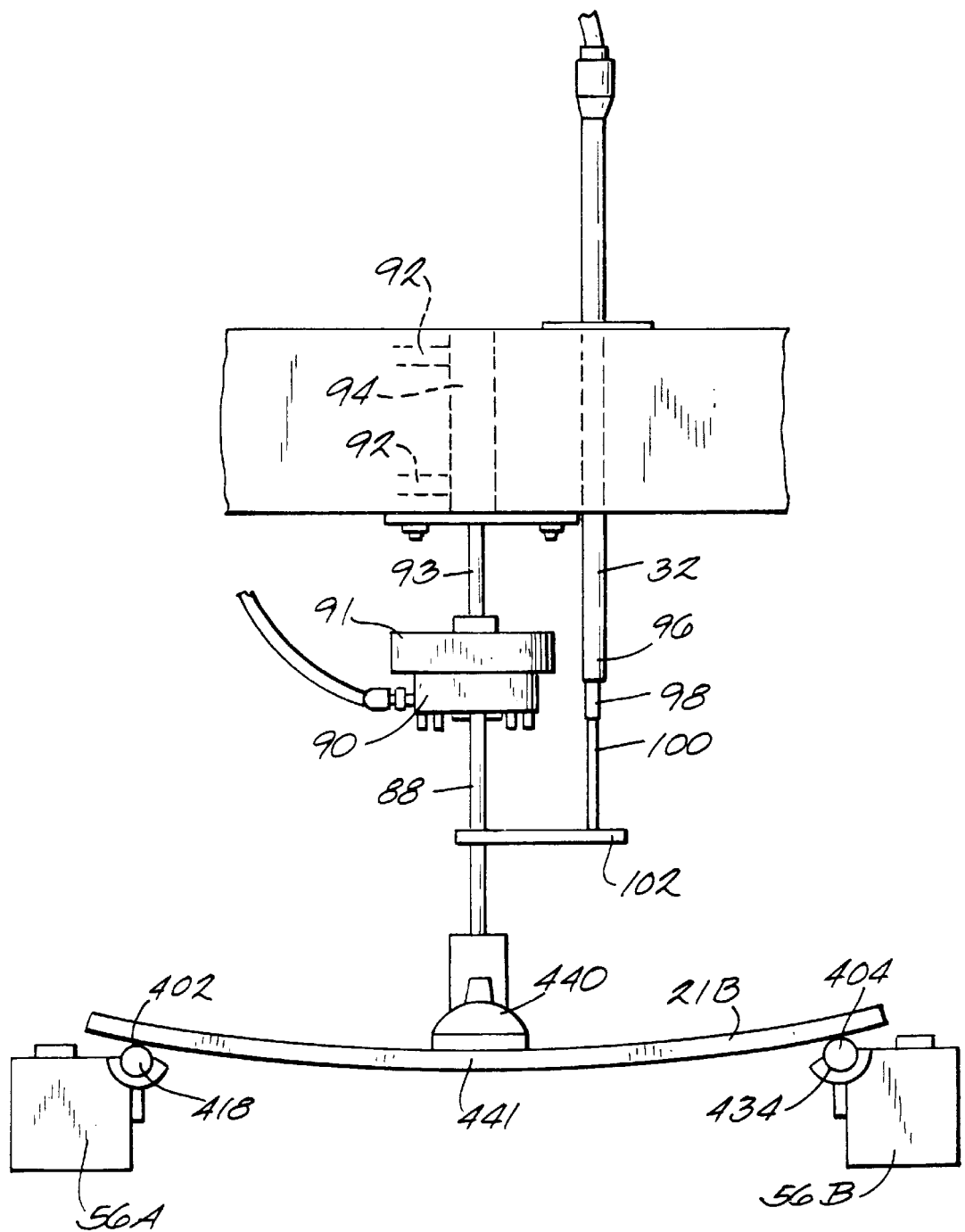
FIG. 14 is a schematic front view of the system in accordance with the present invention, illustrating the bending of the panel illustrated in FIG. 12 for the static bending test.
Figure 15:
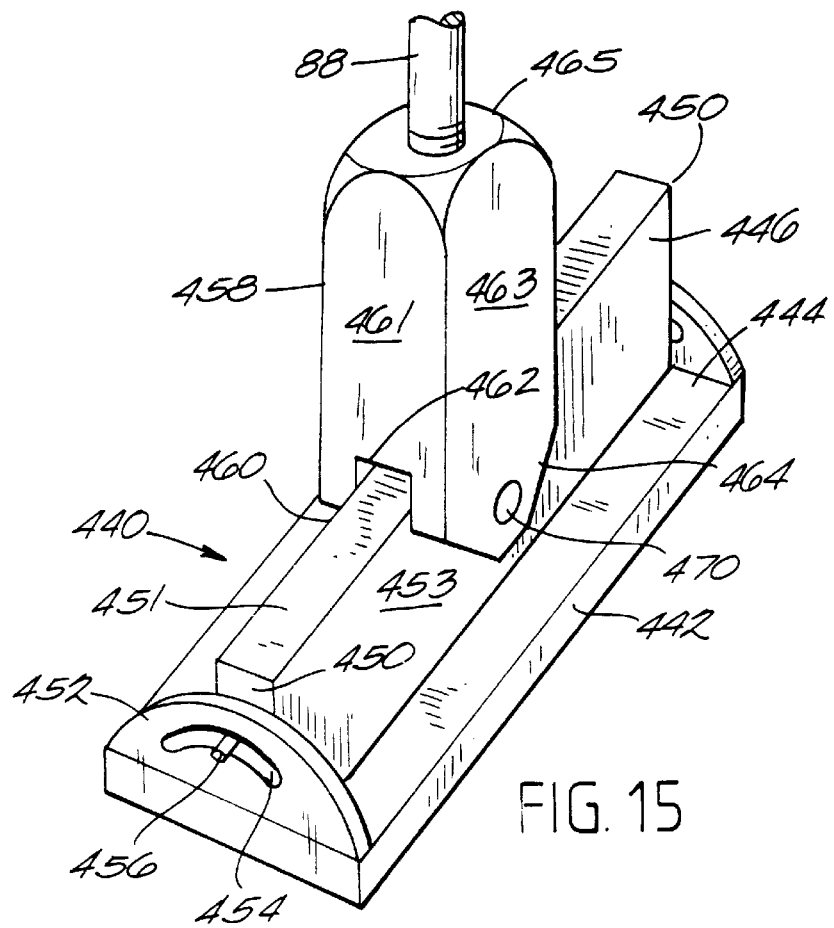
FIG. 15 is a perspective view of the loading bar which contacts the panel to transmit the applied loads in the static bending test, illustrated in FIGS. 12–14.

It is noted that in the static bending test, the support rollers and loading block are constructed so that no appreciable compression of the test panel occurs. This is generally achieved if the radius of the support rollers and the loading block are at least 1½ the thickness of the panel being tested. Jigs 56A and 56B are positioned such that the span for the test is 24 times the nominal thickness of the test panel. The test panel is centered in the span, and the load is applied continuously at midspan 441 throughout the test by a uniform motion of the movable loading block at a rate (mm/min) calculated by the following formula:

$$\text{speed (mm/min)} = 0.48 t$$

wherein t is the nominal thickness of the test panel 21 B. The bending of panel 21B in the static bending test is illustrated in FIG. 14.

Figure 17:
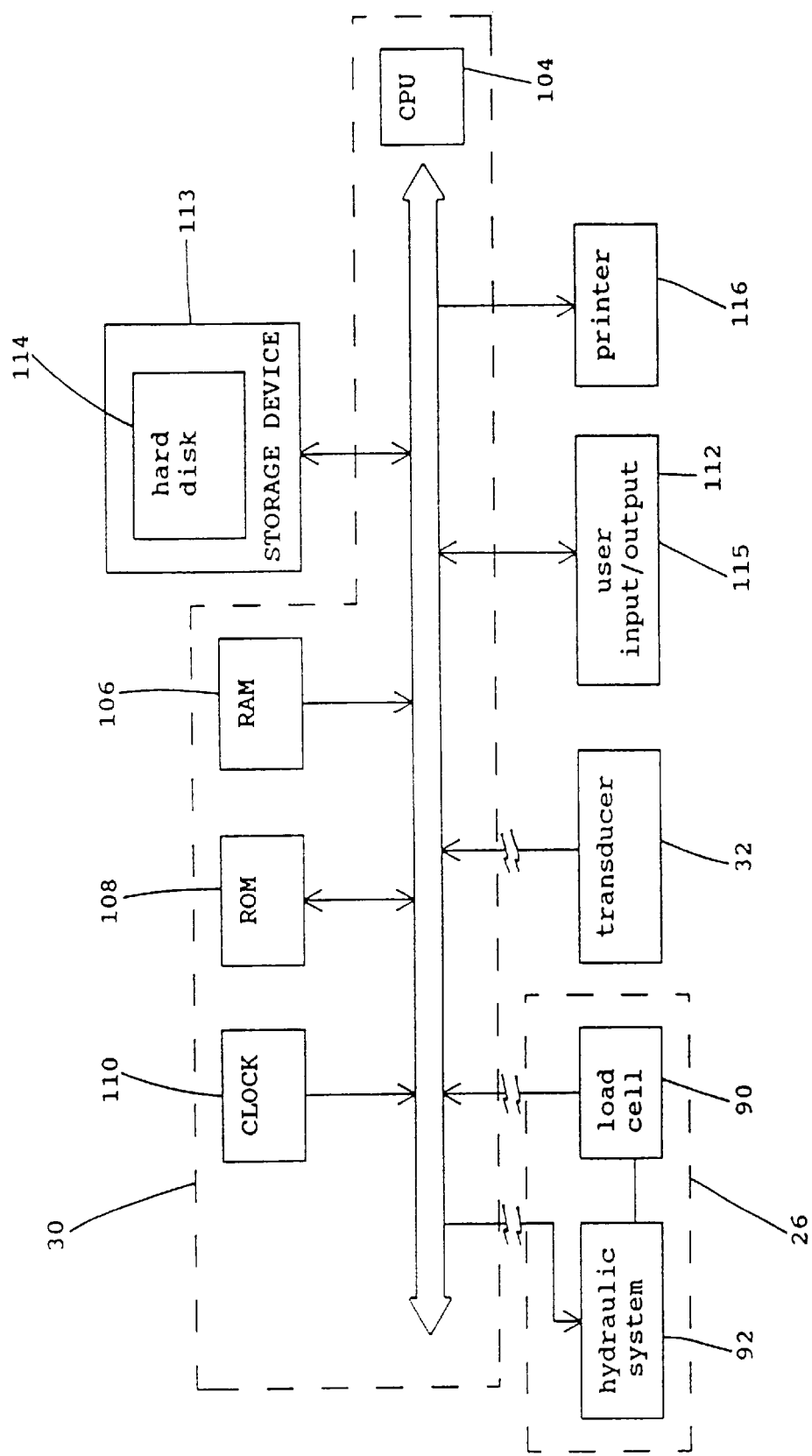
FIG. 17 is a block diagram of the computer system that may be employed in accordance with the present invention.
Figure 18:
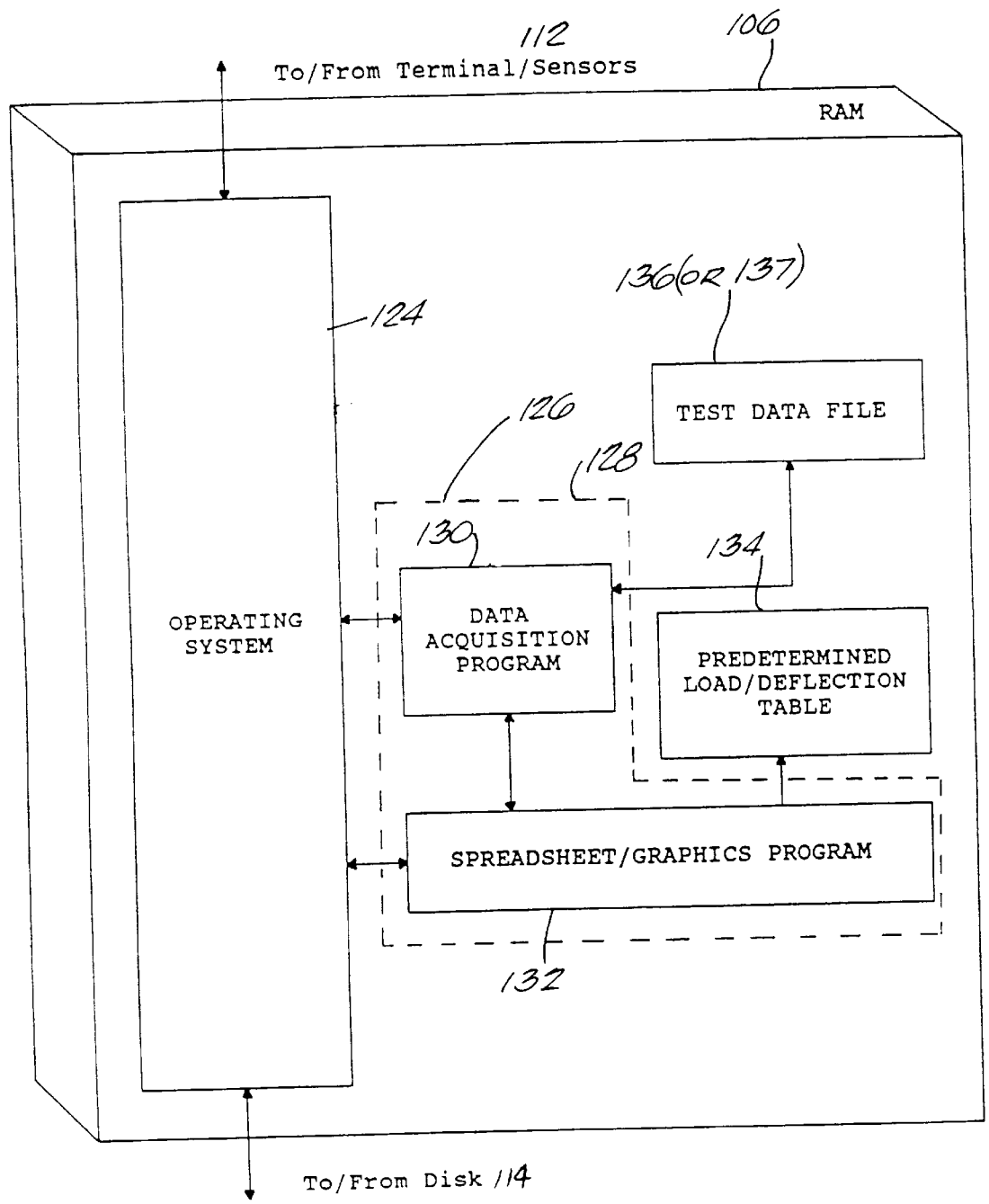
FIG. 18 is a block diagram of the operation of the RAM of FIG. 17 in accordance with the present invention.

Reference is now made to FIGS. 17 and 18 wherein the hardware and software components of computer 30 of the system 20 in accordance with the present invention are depicted in block diagram. The hardware of computer 30 includes a central processing unit (CPU) 104, a random access memory (RAM) 106, a read only memory (ROM) 108, and a clock 110. Computer 30 is also operatively connected to a user input/output device 115, i.e., terminal 112, storage devices 113, e.g., hard disk 114, a printer 116 and a data acquisition and control unit 117. Terminal 112 includes a keyboard 118 and a monitor 120, such as an SVGA monitor. Additionally, computer 30 is operatively connected, i.e., electrically connected, with hydraulic system 92, load cell 90 and transducer 32. The hardware is pictorially represented in FIG. 1. It is evident that the computer is a standard off-the-shelf item having the conventional components, e.g., an IBM compatible computer with 486/66 MHz microprocessor and 8 MB RAM. Unit 117 is an amplifier, D/A converter and interface unit which receives, conditions, converts and passes signals from the load cell, hydraulic system via the proportional relief valve, and the transducer to the computer 30 to CPU 104 where they are acted upon by software portion 126 of system 20 fetched from RAM 106 and necessary information for system operation from ROM 108. Such units are available commercially, e.g., Sciemetric Series 7000 Data Acquisition and Control units.

As seen in FIG. 18, RAM 106 contains a conventional operating system 124, e.g., MS-DOS with a Windows™ environment, both commercially available from Microsoft, Inc., including a system program for loading the software portion 126 of the system in accordance with the present invention into the computer. The software portion 126 of the system is suitably stored in the secondary storage medium, e.g., hard disk 114, for reading by the computer in the conventional fashion. Software 126 includes a load/deflection program 128. The software portion 126 of the system 20 in effect reconfigures the computer to perform a number of functions, detailed hereinafter.

Program 128 suitably includes a data acquisition program 130 such as WinGen™ available from Sciemetric Instruments of Nephean, Ontario, Canada, and a spreadsheet/graphics program 132 such as Microsoft Excel™ available from Microsoft, Inc. In a preferred embodiment, WinGen™ operates as a macro in the Excel™ environment. Software portion 126 further includes a data table 134 of data records of established standards which include, for example, for wood-bases panels, end use/span rating, ultimate load, and maximum permitted deflection at 200 lbs for panels to be tested.

The data acquisition program 130, responsive to data entry respecting the panel to be tested, controls the hydraulic system and application of the load to the panel, and permits signals to be input into the computer from sensors, i.e., load cell 90 and transducer 32, and stores the signals as measured test data records in a test data text file 136 of measured test data. The measured test data are then processed by the program 132 to provide a graphic representation of measured load versus measured deflection, which can be displayed on monitor 120 or provided as a hard copy via printer 116.

The program 132 also generates in tabular summary report form for the concentrated static load test which includes the deflection load, the actual deflection, the permitted maximum deflection and the test result, e.g., pass or fail, as shown in FIG. 14. For the static bending test, the measured test data, i.e., deflection load and actual deflection, is processed to calculate the modulus of elasticity (MOE), the modulus of rupture (MOR), the bending stiffness (EI) and the internal bond (IB). These calculations are described hereinafter. A summary report of these calculated values is generated.

Reference is now made to FIGS. 19–27, wherein flowcharts illustrate the logical steps involved in testing a panel in accordance with the present invention. Testing of the panel is done in three ways—the concentrated load test, the ultimate load test, and the static bending test. From the latter, the modulus of elasticity, modulus of rupture, bending stiffness and internal bond are calculated and reported.

Figure 19:
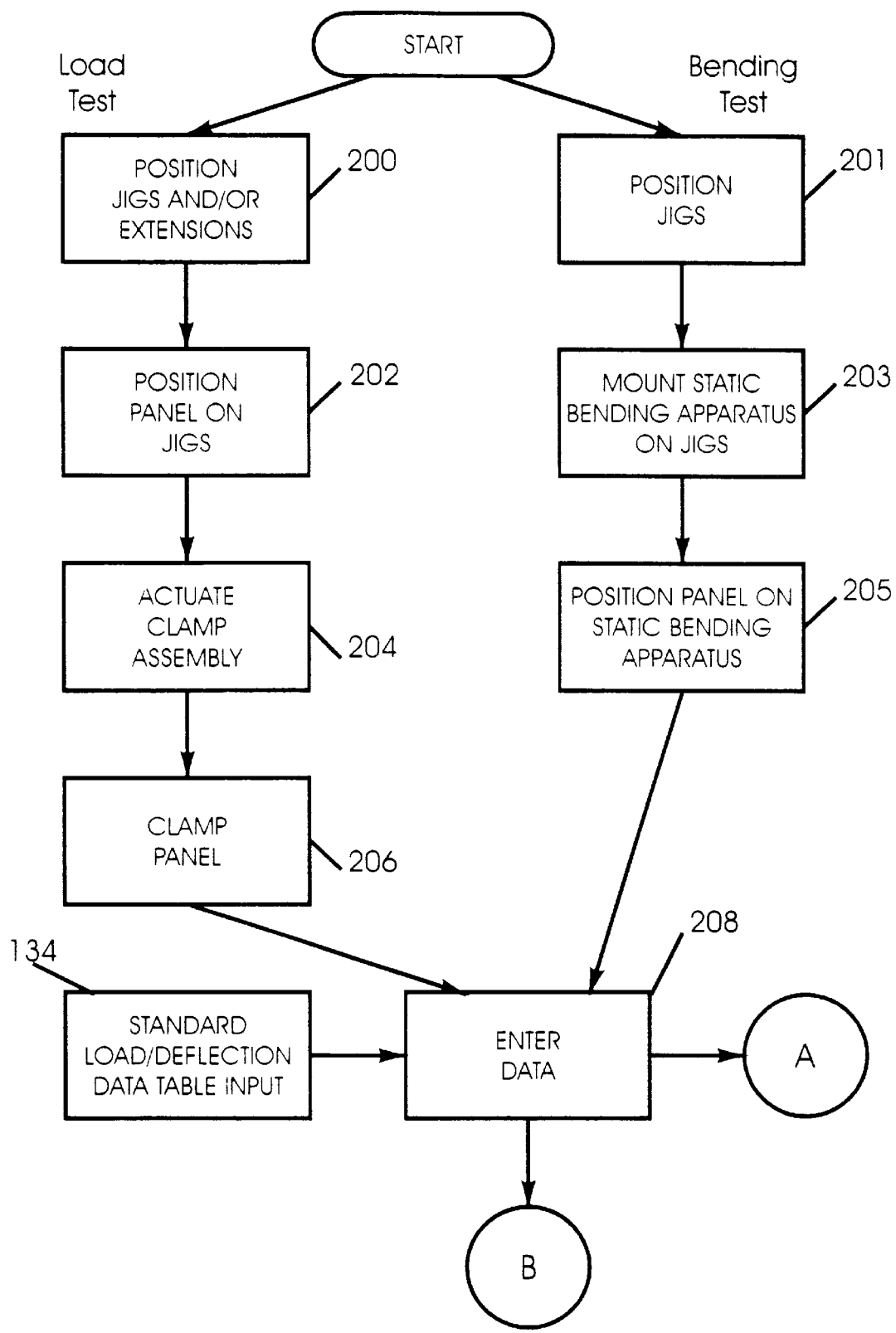
FIG. 19 is a flowchart illustrating the concentrated static load and static bending testing in accordance with the present invention, including a program for the computer in the system of FIG. 1.

As seen in FIG. 19, to test a panel for the concentrated load and ultimate load tests in accordance with system 20, the overall system begins at step 200 with positioning of the jigs, i.e., clamps 50, 52 and 54 are spaced apart depending on the end use of the panel 21 and the span rating, e.g., roofing panel rated "16" will be placed on horizontal section 30 with the clamps 50, 52 and 54 spaced 16 inches apart. System 20, including jig and top portion extensions, can handle sheets up to 48 inches wide and up to 96 inches long. The clamps can be readily spaced to all span ratings from "16" inches to "48" inches. At step 202, panel 21 to be tested is set horizontally on support section 38 to rest on jigs 56 and against a panel stop 61.

At step 204, the clamp assembly 24 is actuated via air regulator 89 to admit air through line into hose 74, and at step 206, panel 21 is clamped into test position as hose 74 expands due to the influx of air and presses T-plate 76 downward with cylindrical pins 80 pressing and holding panel 21.

At step 208, data regarding the panel to be tested is entered as detailed further hereinafter in "A" of FIG. 20. As seen in FIG. 21, at step 210, performance standard load data, i.e., ultimate load, is selected from data table 134 according to the panel to be tested, and at step 212, the hydraulic system is actuated and loading disk 86 is placed on panel 21. In turn, at step 214, the predetermined load is applied through loading disk 86 to the panel 21. At step 216, the deflection under the load is measured, more properly the deflection is measured as a function of the load as the load is increased to a predetermined standard ultimate load. At step 218, the load/deflection test data are stored in data file 136.

Once the ultimate load has been applied, at step 219, hose 74 is deflated by throwing a release switch to release the air from hose 74, and hose 74, plate 72 and T-plate 74 are again pressed against the face 70 of top portion 58 via springing action of springs 78.

It is noted that if a full size panel (4 ft.×8 ft.) is being tested, jig extension and top portion extensions are attached to clamps 50, 52 and 54 in the manner described hereinbefore. Hose 370 is connected into the pneumatic system 79, and is inflated and deflated in synchrony with hose 74.

Load and deflection test data are received by the computer via a load indicating signal from the load cell and a deflection indicating signal from the transducer, respectively. As described previously, the computer is also programmed to actuate the hydraulic system to apply the predetermined load.

Figure 20:
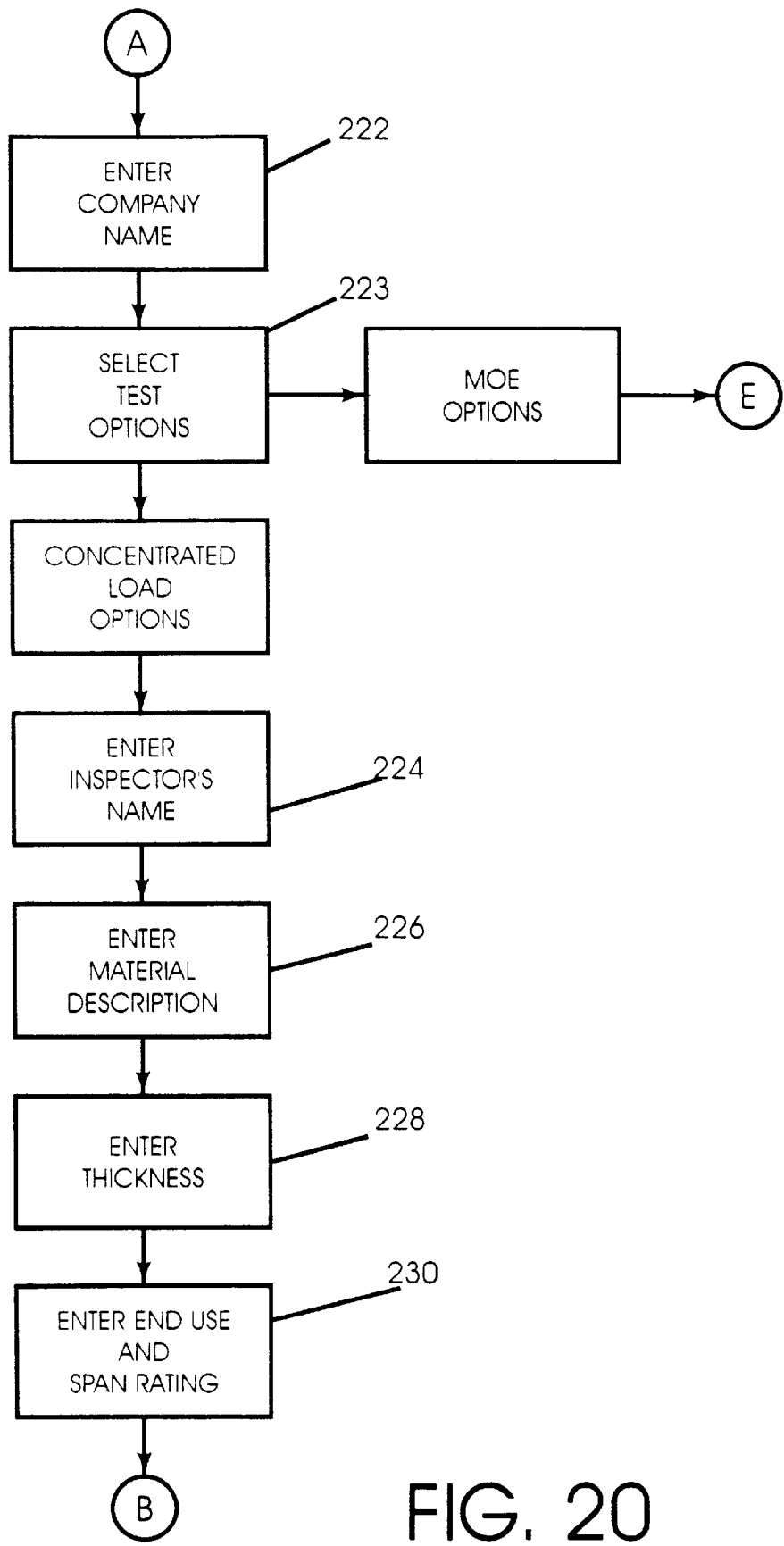
FIG. 20 is a flowchart illustrating data entry logic of the computer program in accordance with the present invention, particularly for the concentrated load options.

As seen in FIG. 19, data entry step 208, beginning at "A", includes several steps including test selection as shown in FIG. 20. At step 208, as illustrated in FIG. 19, a data entry screen appears on the monitor, and at step 222, as seen in FIG. 20, the company/manufacturer name is entered and at step 223, test options are selected. A sample screen menu is illustrated in FIG. 27. If the static bending test, i.e., MOE options, is selected, this option is detailed at "E" of FIG. 23.

If concentrated load options are selected, at step 224, the inspector's name is entered. Optionally, this entry is simply selected from a list of end uses and ratings, by highlighting the desired entry; a sample data entry screen is illustrated in FIG. 28. At step 226, the material description is entered or selected from a list, e.g., plywood or OSB. At step 228, the thickness of the panel is entered, typically in inches. At step 230, the end use and span rating of the panel to be tested is entered. The computer then commences the test by looking up the predetermined loads in the lookup data table 134, actuating the hydraulic system to apply the appropriate load, actuating the transducer to read the deflection, and receiving the deflection indicating signal from the transducer, as described hereinbefore. At the end of the test, i.e., once the ultimate load has been applied, the computer deactuates the hydraulic system at step 219, as shown in FIG. 21, and a report, as shown, e.g., in FIG. 26, is printed.

Concentrated load testing of the panel is reported in two ways-the concentrated load test and the ultimate load test. Suitable logic for the concentrated load test is illustrated in FIG. 22 beginning at "C". At step 232, maximum permitted deflection at 200 lbs. is retrieved from the performance standard data table 134; at step, 234, the measured deflection at 200 lbs. is retrieved from test data file 136. At step 236, a test is performed to compare the maximum permitted deflection at 200 lbs. to the deflection measured to determine if the measured deflection is greater than the permitted deflection. If the answer is "no," then the panel is indicated to "pass" the test at step 238. If the answer is "yes," then the panel is indicated to "fail" the test at step 240.

Suitable logic for the ultimate load test is illustrated in FIG. 22 beginning at "D". At step 242, the ultimate load data is retrieved from performance standard data table 134, and at step 244, the measured deflection at ultimate load is retrieved from the test data file 136. At step 246, a test is performed to determine if the panel withstood the ultimate load, in effect, if the measured load at ultimate is greater than just prior to ultimate load, i.e., if the panel breaks under ultimate load, the measured load decreases. If the answer is "yes," then the panel is deemed to have passed the test at step 248; if the answer is "no," then the panel is deemed to have not passed the test at step 250. A report is then printed at step 252 as illustrated in FIG. 22. FIG. 31 is a report wherein the panel tested failed the ultimate load test. The failure is also represented on the graph of load versus deflection wherein the load abruptly decreases as the panel fails under the load. To test an edge support system such as a tongue and groove system, the panels 21 and 21A are placed and clamped into apparatus 20 as described hereinabove. An ultimate load test is performed using the logic illustrated in FIG. 22 at "D".

Referring again to FIG. 19, to test a panel for bending strength test in accordance with system 20, the overall system begins at step 201 with positioning of two jigs, i.e., jigs 56A and 56B are spaced apart depending on the thickness of panel 21B to be tested. The span is calculated as 24 times the nominal thickness of the panel. For example, if the nominal thickness of the panel is 23/32, the span is calculated as (24×23/32)=17.25 in. At step 203, the static bending apparatus 406 is installed on opposing sides of the jigs 56A and 56B, as explained hereinbefore, with support rollers 418 and 434. At step 205, panel 21B of such nominal thickness is placed on horizontal section 30 with the jigs 56A and 56B spaced 17.25 inches apart. Panel 21B is supported proximate its lateral edges 402 and 404 by support rollers 418 and 434, respectively. That is, panel 21 rests solely on support rollers 418 and 434. Panel 21B is not clamped in any way to clamps 50 and 52. At step 208, data entry occurs.

As seen in FIG. 23, data entry for the bending test is shown at "E". At sample data entry screen is illustrated in FIG. 30. At step 500, the inspector's name is entered. At step 502, the material description is entered or selected from a list, e.g., plywood or OSB. At step 504, the nominal thickness (t) of the panel is entered, typically in inches. At step 506, the width (b) of the panel is entered. At step 508, the span (L) (determined as explained hereinbefore) is entered. At step 509, the length (d) of the panel is entered. At step 504, the thickness is entered. Optionally, the entries at steps 502, 504, 506, 508 and 509 are simply selected from a list which has been previously entered into a program file.

As seen in FIG. 23, beginning at "F", the computer then commences the test by calculating the speed at which the load is continuously applied to the test panel according to the nominal thickness of the panel as shown in the formula given hereinbefore, actuating the hydraulic system, at step 510. At step 512, a load is applied continuously to panel 21B through loading bar 440, placed on panel 21B across its width at the mid-span between the lateral ends of the panel at the speed (mm/min) of 0.48 t where t is the thickness. At step 514, the deflection is measured as a function of the load as the load is increased up to failure or rupture. At step 516, the measured load and deflection data are stored in date file 137. At the end of the test, i.e., once rupture has occurred, the computer deactuates the hydraulic system, and at step 517, a report is generated with the calculated MOE, MOR, EI and IB values. The report is similar to that shown, e.g., in FIG. 31, but detailing MOE, MOR, EI and IB values derived from the test. Suitable logic for the MOE is given at "H" of FIG. 25; suitable logic for the MOR is given at "G" of FIG. 24. Suitable logic for the EI is given at "J" of FIG. 26, and suitable logic for the IB is given at "I" of FIG. 27.

Referring to FIG. 24, beginning at "G", the calculation of MOR is illustrated. At steps 518, 520, 522, the span L, the thickness t, and the width b retrieved, respectively, are retrieved from data file 137. After step 522, calculation of MOE can be effected as illustrated at "H" in FIG. 24. At step 524, the ultimate failure load $P_{max}$ is retrieved from data file 137. After step 524, calculation of IB can be effected as illustrated at "I" in FIG. 27.

At step 526, the MOR is calculated from equation $$MOR = \frac{3P_{max}L}{2bt^2}$$

At step 528, the calculated MOR can be displayed on a screen.

Suitable logic for the MOE test is illustrated in FIG. 25, beginning at "H". The data values are retrieved as in steps 518, 520 and 522. At step 534, the slope, $\Delta p/\Delta y$, of the load/deflection measurement is determined using two points, i.e., $\Delta p/\Delta y=P_2-P_1/y_2-y_1$, in the range where load and deflection are proportional, e.g., see the linear portion of the graph in FIG. 32. At step 536, the MOE is calculated from the equation $$MOE = \frac{L^3}{4bt^3} \cdot \frac{\Delta p}{\Delta y}$$

Optionally, the calculated MOE can be displayed at step 538.

Suitable logic for calculating bending stiffness (EI) is given in FIG. 26, beginning at "J". From steps 518 and 534, the span L and the slope, $\Delta p/\Delta y$, are retrieved. At step 540, the EI is calculated from equation $$EI = \frac{L^3}{192} \cdot \frac{\Delta p}{\Delta y}$$

Optionally, the calculated EI can be displayed at step 542.

Suitable logic for calculating internal bend (IB) is given in FIG. 27, beginning at "I". From steps 522 and 524, the width and the maximum load applied $P_{max}$ are retrieved. At step 544, the length d is retrieved, and at step 546, the IB is calculated from the equation $$IB = \frac{P_{max}}{db}$$

Optionally, the calculated IB can be displayed at step 548.

Security is suitably built into the program by providing unchangeable numbering of the test reports.

The present invention is further explained by the following examples which should not be construed by way of limiting the scope of the present invention.

The following examples show the actual testing of a wood panel in accordance with ASTM E661-88, Standard Test Method for Performance of Wood and Wood-Based Floor and Roof Sheathing Under Concentrated Static and Impact Loads, incorporated herein by reference.

EXAMPLE 1

The present apparatus was operated in accordance with the following specific conditions.

An OSB sample which was subfloor panel and span rated at 16 inches was chosen and placed on the support assembly with the clamp members spaced 16 inches apart from each other. The sample was 24 inches wide and had a thickness of 23/32 inch.

Appropriate data entry for the panel was effected and the program run, and a load applied up to the ultimate load of 400 lbs. (according to Department of Commerce Standard PS-2). For the load deflection test, the actual deflection was read at 201 lbs. to be 0.214 inch. The permitted maximum deflection is 0.250 inch, per PS-2. The panel passed the quality assurance load deflection test.

For the ultimate load test, the program determines if the panel load maintains through the ultimate load, in this case, 400 lbs. It was determined that the panel withstood the ultimate load as evidence by the graph shown in FIG. 32.

EXAMPLE 2

The present apparatus was operated in accordance with the following specific conditions.

An OSB sample which was roofing panel and span rated at 24 inches was chosen and placed on the support assembly with the clamp members spaced 24 inches apart from each other. The sample was 24 inches wide and had a thickness of 7/16 inch.

Appropriate data entry for the panel was effected and the programmed load test was run. The actual deflection was found to be 0.407 inch for a load of 200 lbs. The permitted maximum deflection is 0.469 inch. The panel passed the quality assurance load deflection test.

As described in Example 1, the ultimate load test was run. Similar to Example 1, the ultimate load to be applied to the test panel is 400 lbs. As seen in FIG. 31, the panel failed at a 386-lb. load and hence, failed the test, i.e. measured load decreased after 386 lbs.

EXAMPLE 3

The present apparatus was operated in accordance with the following specific conditions.

An OSB sample which is a roofing panel with a thickness of 7/16 in. is chosen and placed on the static bending support assembly 406 with jigs 56A and 56B (i.e., the left and middle jigs) positioned 10.5" apart. The length of the panel should be 2" longer than the span. The test specimen is placed on rollers 418 and 434 so that it is centered under the loading block 440.

Appropriate data is entered for the panel including the width of the specimen and whether the grain is parallel or perpendicular to the length. The programmed test is run until the specimen breaks. The loading block automatically retracts, and a test report is printed.

In summary, the present invention provides panel performance test system which eliminates the costs and difficulties associated with weekly shipping of products to remote laboratories for testing. The system provides the ability to perform quality control testing in-house, at the mill, for each product run and correct any performance problems virtually immediately. As such, manufacturers have the confidence that their products are meeting quality control standards, and assures the manufacturer's reputation for quality.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

I claim:

1. A panel performance testing system, comprising:

a support frame, a load-applying assembly, a clamping assembly, a linear measurement device, and a computer;

said support frame for supporting and clamping a non-moving panel to be tested; said frame comprising a horizontal support section supporting said clamping assembly;

said clamping assembly for supporting a first major surface of the panel along spaced apart parallel frame members extending substantially across the width of the panel and clamping against a second opposite major surface of the panel along the spaced apart parallel frame members extending substantially across the width of the panel; said clamping assembly including three substantially C-shaped clamps, each of said clamps having a bottom frame member and a releasable bottom frame extension for supporting said first major surface of the panel and a top portion and a releasable top portion extension for clamping against said second major surface of the panel;

said load-applying assembly supported on said support frame for applying a load to said second major surface of the panel, said load-applying assembly including a load cell for developing and transmitting a load-indicating signal corresponding to the applied load;

said linear measurement sensor for measuring the magnitude of deflection of the panel under the applied load; said sensor comprising a linear displacement transducer for developing and transmitting a deflection-indicating signal corresponding to the deflection of the panel and a failure-indicating signal corresponding to rupture of the panel under the applied load;

said computer operatively connected to said load cell and said transducer, and configured to receive and process said load-indicating signal and said deflection-indication signal into data records of test loads, deflections and ruptures.

2. The system of claim 1, wherein said load-applying assembly is an hydraulically actuated system having an hydraulic ram, a universal joint, a rod, and a loading disk, said ram for applying the load, said load cell contacting said ram, said rod connecting said load cell to said universal joint and said loading disk connected to said universal joint and contacting the panel to be tested.

3. The system of claim 1, wherein said loading disk is a loading block, said loading block capable of applying a uniform load across the width of the panel.

4. The system of claim 1, wherein said bottom frame member of each said clamp has a substantially flat bottom member front face, and said top portion of each said clamp has a substantially flat top portion front face, an elongate, substantially rectangular bottom surface, a first plate beneath said bottom surface, a second plate beneath said first plate and a hose sandwiched between said first plate and said bottom surface; said second plate coextensive with said first plate and having a flat, substantially rectangular elongate top member and a downwardly depending perpendicular member having a plurality of protruding, linearly aligned and spaced apart pins; said hose operatively connected to a pneumatic system for inflating and deflating said hose.

5. The system of claim 4, wherein:

said releasable bottom frame extension includes a front end and a back end, said back end of said bottom frame extension releasably attached to said bottom frame front face of said bottom frame member, and said releasable top portion extension includes a front end, a back end, a second elongate, substantially rectangular bottom surface, a presser plate beneath said second bottom surface, a pinner plate beneath said presser plate of said second bottom surface and a second hose sandwiched between said first plate and said second bottom surface; said second plate coextensive with said first plate and having a flat, substantially rectangular elongate top member and a downwardly depending perpendicular member having a plurality of protruding, linearly aligned and spaced apart pins; said back end of said top portion extension releasably attached to said top portion front face of said top portion of each said clamp; said second hose operatively connected to said pneumatic system for inflating and deflating said second hose in synchrony with said first hose.

6. A static bending measuring system for a wood-based panel, comprising:

a hydraulic subsystem for applying a continuous load to a non-moving panel to be tested up to a rupture load;

a load cell, operatively associated with the hydraulic subsystem, for measuring the applied load;

a linear displacement transducer for measuring a deflection of the panel under the applied load; and a computer for storing and executing a load/deflection measuring program, and at least one input device, and operatively coupled to the hydraulic subsystem, said load cell and said transducer, for recording and processing data relating to the applied load and the corresponding displacement, said computer having a central processing unit, a memory medium and data storage means for storing data records; said computer comprising said load/deflection measuring program in execution on said computer for controlling a static bending test; said program, operatively communicating with said central processing unit, memory and data storage, for controlling the applied load, receiving displacement-indicating signals from said transducer and load-indicating signals from said load cell, receiving a rupture-indicating signal from said load cell, processing the load-indicating signals, the displacement-indicating signals and the rupture-indicating signal to derive test data of applied load, measured deflection corresponding to the applied load, and a maximum load, and using the test data to compute a measure of the bending of the panel.

7. The system of claim 6, wherein said measure of bending is an MOE, MOR, IB, EI or a combination thereof.

8. The system of claim 7, wherein said computer further processes said measure into a printed test result report.

9. A method of testing the bending of a panel under an applied load, said method comprising the computer-assisted steps of:

applying a continuous uniform load to a first major surface of the non-moving panel up to a rupture load, a second opposite major surface of the panel supported at its lateral edges at a predetermined span interval depending upon the nominal thickness of the panel, measuring deflections of the panel upon application of the load and developing deflection-indicating signals corresponding to deflections;

measuring said applied load corresponding to the deflections and developing load-indicating signals corresponding the said applied load;

measuring said applied load at the rupture of the panel and developing a maximum load-indicating signal;

interpreting said load-indicating signals, said deflection-indicating signals and said maximum load-indicating signal to derive test data of the bending of the panel; and printing a report of the test data.

10. An apparatus for measuring bending of a panel material under application of a continuous standard load, the panel having a width, a length and a depth, said apparatus comprising:

first and second roller bearing supports for supporting a first major surface of a panel at two spaced apart finite locations;

a load-applying assembly for imparting a continuous uniform load to a second opposite major surface of the panel across the width of the panel midway between said first and second supports, said assembly comprising a loading block and an hydraulic means for applying force to said loading block;

a load cell operatively connected to said loading block for measuring the load applied through said loading block imparted to the panel, said load cell developing and transmitting load-indicating signals corresponding to said applied load and a rupture-indicating signal corresponding to rupture of the panel under the applied load;

a transducer operatively connected to said load-applying assembly for measuring a displacement of the assembly upon applying load to the panel, said displacement corresponding to a deflection sustained by the panel as a result of the applied load, said transducer developing and transmitting a displacement-indicating signals corresponding to said displacement;

a computer for storing and executing a load/deflection measuring program and having a display and at least one user input device, and operatively coupled to said load-applying assembly, said load cell and said transducer for recording and processing data relating to said applied load and said displacement, said computer having a central processing unit, a memory medium and data storage means for storing data records, said load/deflection measuring program in execution on said computer for controlling a static bending test, said program, operatively communicating with said central processing unit, memory and data storage means, for controlling the applied load, for receiving said displacement-indicating signals, said corresponding load-indicating signals and said rupture-indicating signal, for processing said displacement-indicating signals, said load-indicating signals and said rupture-indicating signals to derive test data of applied load, measured deflection and maximum load, and using said test data to compute a measure of the bending of the panel.

11. A method of testing edge support systems for joining panels together by applying load to the system, said method comprising the steps of:

storing in a data table in a memory medium, predetermined standard load and deflection parameters corresponding to end use and span rating of panels;

entering end use and span rating data for panels to be tested;

supporting first and second panels at first, second and third supports spaced apart at finite locations, said first and second panels being joined at edges forming an edge support joint;

clamping said joined panels at said first, second and third supports; said clamping including, for each support, (i) positioning above each support a hose and a plate having a plurality of protruding pins, positioned and secured to the bottom of said hose, (ii) inflating and expanding said hose, and thereby (iii) displacing downward said plate until said pins contact and penetrate the panel;

determining a predetermined standard load for the panels to be tested depending upon the end use and span rating and a corresponding standard deflection;

imparting the standard load to said joined panels midway between said first and second supports and proximate said edge support joint;

measuring the load applied to the panel and developing a load-indicating signal corresponding the said applied load;

measuring a deflection of the joined panels as a result of applying the load to said joined panels, and developing a deflection-indicating signal corresponding to the measured deflection;

interpreting said load-indicating signal and said deflection-indicating signal to derive test data of applied load and measured deflection;

analyzing said measured deflection and said predetermined standard deflection to determine whether the measured deflection of the panel is greater than the standard deflection;

providing a test result; and printing a report of the test result.

12. The system of claim 11, further comprising a clamping assembly for supporting and clamping the panel; said clamping assembly for supporting a first major surface of the panel along spaced apart parallel frame members extending substantially across the width of the panel and clamping against a second opposite major surface of the panel along the spaced apart parallel frame members extending substantially across the width of the panel; said clamping assembly including three substantially C-shaped clamps, each of said clamps having a bottom frame member and a releasable bottom frame extension for supporting said first major surface of the panel and a top portion and a releasable top portion extension for clamping against said second major surface of the panel.

13. The system of claim 12, wherein said bottom frame member of each said clamp has a substantially flat bottom member front face, and said top portion of each said clamp has a substantially flat top portion front face, an elongate, substantially rectangular bottom surface, a first plate beneath said bottom surface, a second plate beneath said first plate and a hose sandwiched between said first plate and said bottom surface; said second plate coextensive with said first plate and having a flat, substantially rectangular elongate top member and a downwardly depending perpendicular member having a plurality of protruding, linearly aligned and spaced apart pins; said hose operatively connected to a pneumatic system for inflating and deflating said hose.

14. The system of claim 13, wherein:

said releasable bottom frame extension includes a front end and a back end, said back end of said bottom frame extension releasably attached to said bottom frame front face of said bottom frame member, and said releasable top portion extension includes a front end, a back end, a second elongate, substantially rectangular bottom surface, a presser plate beneath said second bottom surface, a pinner plate beneath said presser plate of said second bottom surface and a second hose sandwiched between said first plate and said second bottom surface; said second plate coextensive with said first plate and having a flat, substantially rectangular elongate top member and a downwardly depending perpendicular member having a plurality of protruding, linearly aligned and spaced apart pins; said back end of said top portion extension releasably attached to said top portion front face of said top portion of each said clamp; said second hose operatively connected to said pneumatic system for inflating and deflating said second hose in synchrony with said first hose.

15. A panel performance testing system, comprising:

a support frame, a load-applying assembly, a clamping assembly, a linear measurement device, and a computer;

said support frame for supporting and clamping a panel to be tested; said frame comprising a horizontal support section supporting said clamping assembly;

said clamping assembly for supporting a first major surface of the panel along spaced apart parallel frame members extending substantially across the width of the panel and clamping against a second opposite major surface of the panel along the spaced apart parallel frame members extending substantially across the width of the panel; said clamping assembly including three substantially C-shaped clamps, each of said clamps having a bottom frame member and a releasable bottom frame extension for supporting said first major surface of the panel and a top portion and a releasable top portion extension for clamping against said second major surface of the panel, wherein said bottom frame member of each said clamp has a substantially flat bottom member front face, and said top portion of each said clamp has a substantially flat top portion front face, an elongate, substantially rectangular bottom surface, a first plate beneath said bottom surface, a second plate beneath said first plate and a hose sandwiched between said first plate and said bottom surface; said second plate coextensive with said first plate and having a flat, substantially rectangular elongate top member and a downwardly depending perpendicular member having a plurality of protruding, linearly aligned and spaced apart pins; said hose operatively connected to a pneumatic system for inflating and deflating said hose;

said load-applying assembly supported on said support frame for applying a load to said second major surface of the panel, said load-applying assembly including a load cell for developing and transmitting a load-indicating signal corresponding to the applied load;

said linear measurement sensor for measuring the magnitude of deflection of the panel under the applied load; said sensor comprising a linear displacement transducer for developing and transmitting a deflection-indicating signal corresponding to the deflection of the panel and a failure-indicating signal corresponding to rupture of the panel under the applied load;

said computer operatively connected to said load cell and said transducer, and configured to receive and process said load-indicating signal and said deflection-indication signal into data records of test loads, deflections and ruptures.

16. The system of claim 15, wherein;

said releasable bottom frame extension includes a front end and a back end, said back end of said bottom frame extension releasably attached to said bottom frame front face of said bottom frame member, and said releasable top portion extension includes a front end, a back end, a second elongate, substantially rectangular bottom surface, a presser plate beneath said second bottom surface, a pinner plate beneath said presser plate of said second bottom surface and second hose sandwiched between said first plate and said second bottom surface; said second plate coextensive with said first plate and having a flat, substantially rectangular elongate top member and a downwardly depending perpendicular member having a plurality of protruding, linearly aligned and spaced apart pins; said back end of said top portion extension releasably attached to said top portion front face of said top portion of each said clamp; said second hose operatively connected to said pneumatic system for inflating and deflating said second hose in synchrony with said first hose.

17. A static bending measuring system for a wood-based panel, comprising:

a hydraulic subsystem for applying a continuous load to a panel to be tested up to a rupture load;

a load cell, operatively associated with the hydraulic subsystem, for measuring the applied load;

a linear displacement transducer for measuring a deflection of the panel under the applied load; and a computer for storing and executing a load/deflection measuring program, and at least one input device, and operatively coupled to the hydraulic subsystem, said load cell and said transducer, for recording and processing data relating to the applied load and the corresponding displacement, said computer having a central processing unit, a memory medium and data storage means for storing data records; said computer comprising said load/deflection measuring program in execution on said computer for controlling a static bending test; said program, operatively communicating with said central processing unit, memory and data storage, for controlling the applied load, receiving displacement-indicating signals from said transducer and load-indicating signals from said load cell, receiving a rupture-indicating signal from said load cell, processing the load-indicating signals, the displacement-indicating signals and the rupture-indicating signal to derive test data of applied load, measured deflection corresponding to the applied load, and a maximum load, and using the test data to compute a measure of the bending of the panel, wherein said measure of bending is an MOE, MOR, IB, EI or a combination thereof.

18. The system of claim 17, wherein said computer further processes said measure into a printed test result report.

* * * * *